(12) United States Patent
Voegele et al.

(10) Patent No.: US 7,753,936 B2
(45) Date of Patent: Jul. 13, 2010

(54) FORM IN PLACE FASTENERS

(75) Inventors: James W. Voegele, Cincinnati, OH (US);
Wells D. Haberstich, Loveland, OH (US); J. Charles Hueil, Loveland, OH (US); John V. Hunt, Cincinnati, OH (US); Ronald J. Kolata, Cincinnati, OH (US); Anil K. Nalagatla, Mason, OH (US); Daniel W. Price, Loveland, OH (US); Christopher W. Widenhouse, Clarksville, OH (US); Craig N. Faller, Milford, OH (US); Bennie Thompson, Cincinnati, OH (US); John W. Sheets, Jr., Bridgewater, NJ (US)

(73) Assignee: Ehticon Endo-Surgery, Inc., Cincinnati, OH (US)

( * ) Notice: Subject to any disclaimer, the term of this patent is extended or adjusted under 35 U.S.C. 154(b) by 632 days.

(21) Appl. No.: 11/558,599

(22) Filed: Nov. 10, 2006

(65) Prior Publication Data

US 2008/0114381 A1 May 15, 2008

(51) Int. Cl.
*A61B 17/08* (2006.01)
(52) U.S. Cl. ................................. 606/215; 606/216
(58) Field of Classification Search ......... 411/501–502, 411/34; 227/175.1; 604/57, 59–62; 606/76, 606/77, 213, 214, 215, 219, 151, 280, 281, 606/71
See application file for complete search history.

(56) References Cited

U.S. PATENT DOCUMENTS

| | | | | |
|---|---|---|---|---|
| 3,223,083 A | * | 12/1965 | Cobey | 606/92 |
| 4,478,544 A | * | 10/1984 | Strand | 411/34 |
| 4,687,395 A | * | 8/1987 | Berecz et al. | 411/361 |
| 4,900,303 A | * | 2/1990 | Lemelson | 604/514 |
| 5,290,281 A | * | 3/1994 | Tschakaloff | 606/28 |
| 5,361,483 A | * | 11/1994 | Rainville et al. | 29/524.1 |
| 5,928,611 A | | 7/1999 | Leung | |

(Continued)

FOREIGN PATENT DOCUMENTS

WO   WO 03/088845   10/2003

OTHER PUBLICATIONS

U.S. Appl. No. 09/430,177, filed Oct. 29, 1999, Narang et al.

*Primary Examiner*—(Jackie) Tan-Uyen T Ho
*Assistant Examiner*—Son Dang
(74) *Attorney, Agent, or Firm*—Frost Brown Todd LLC

(57) ABSTRACT

A fastening device for clamping and fastening tissue together with fasteners formed from an adhesive is disclosed. An embodiment of the adhesive fastening device can clamp a first and a second portion of tissue together between a first and a second jaw, and can place a fluid polymer adhesive into tissue and form it into a polymerized surgical fastener within the tissue. The adhesive fastener can be formed as a polymerized shank or shaft extending through the tissue, and can have one or more heads formed on the shank. The shank can be formed solely from the polymerizable adhesive, or can be formed from another material such as nitinol, titanium, stainless steel, suture, or a plastic. Shanks of other material can be combined with the adhesive. Alternately, an adhesive fastener can be formed extending distally from a distal end of the surgical device. And, an adhesive fastener can be formed around a luminal tissue or within luminal tissue.

16 Claims, 31 Drawing Sheets

U.S. PATENT DOCUMENTS

| | | |
|---|---|---|
| 6,010,054 A | 1/2000 | Johnson et al. |
| 6,024,480 A | 2/2000 | Seaton et al. |
| 6,217,603 B1 | 4/2001 | Clark et al. |
| 6,455,064 B1 | 9/2002 | Narang et al. |
| 6,656,193 B2 | 12/2003 | Grant et al. |
| 6,681,979 B2 | 1/2004 | Whitman |
| 6,727,612 B1* | 4/2004 | Hull et al. .................. 310/68 D |
| 6,905,295 B2* | 6/2005 | Stevenson et al. ............. 411/34 |
| 7,055,730 B2 | 6/2006 | Ehrenfels et al. |
| 7,066,944 B2* | 6/2006 | Laufer et al. ................ 606/151 |
| 7,351,022 B2* | 4/2008 | Denslow ...................... 411/501 |
| 7,416,554 B2* | 8/2008 | Lam et al. ................... 606/153 |
| 7,431,730 B2* | 10/2008 | Viola ......................... 606/219 |
| 7,517,356 B2 | 4/2009 | Heinrich |
| 2002/0165563 A1* | 11/2002 | Grant et al. ................. 606/151 |
| 2004/0190975 A1* | 9/2004 | Goodman et al. ........... 401/134 |
| 2005/0184121 A1* | 8/2005 | Heinrich ................... 227/175.1 |
| 2005/0192628 A1* | 9/2005 | Viola ......................... 606/219 |
| 2006/0239359 A1 | 10/2006 | Savekar et al. |
| 2008/0082114 A1* | 4/2008 | McKenna et al. ........... 606/153 |
| 2008/0308604 A1* | 12/2008 | Timm et al. ............... 227/175.1 |

* cited by examiner

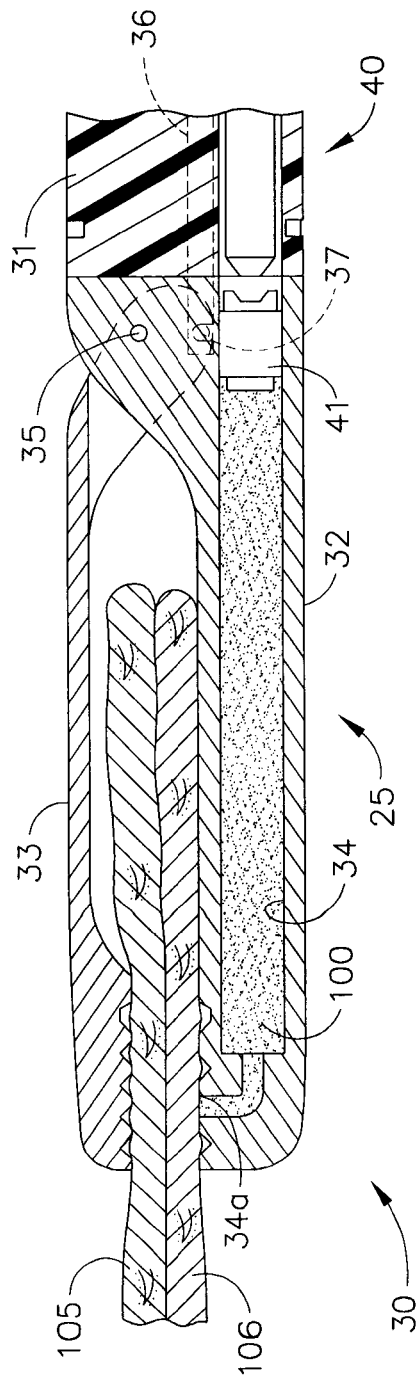
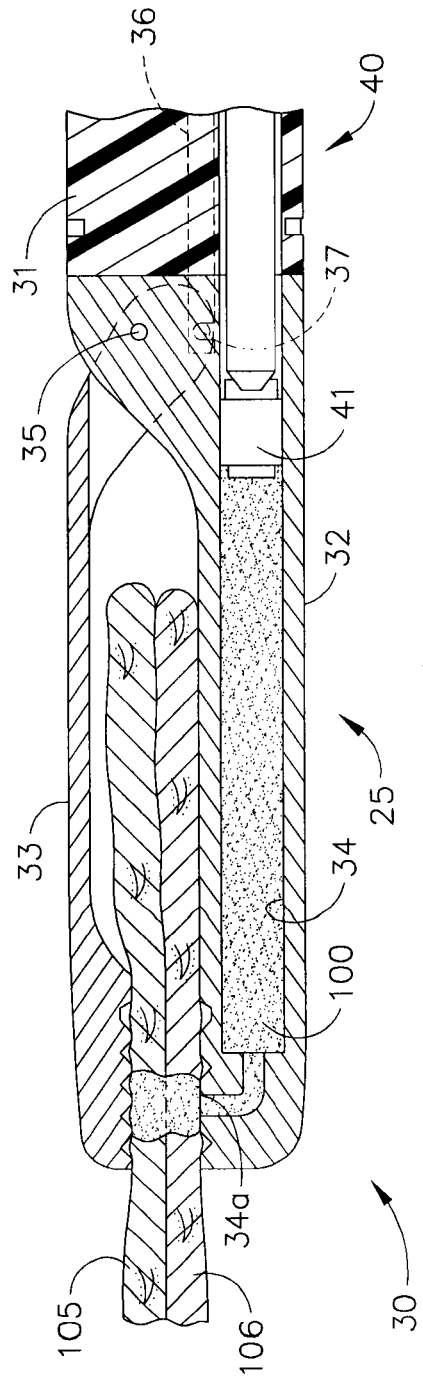
FIG. 1a
FIG. 1b

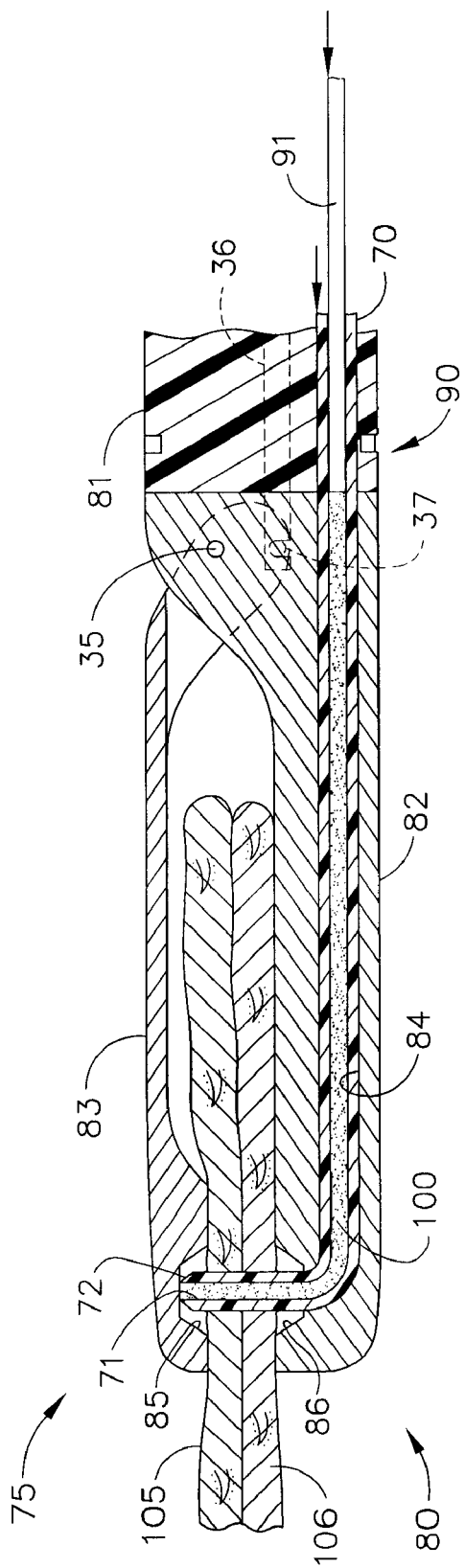

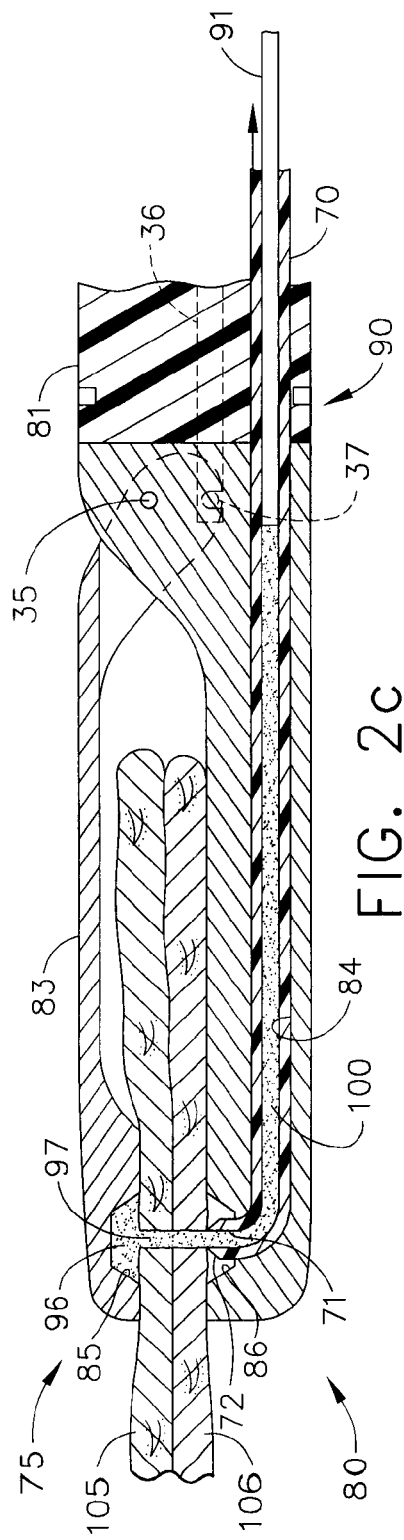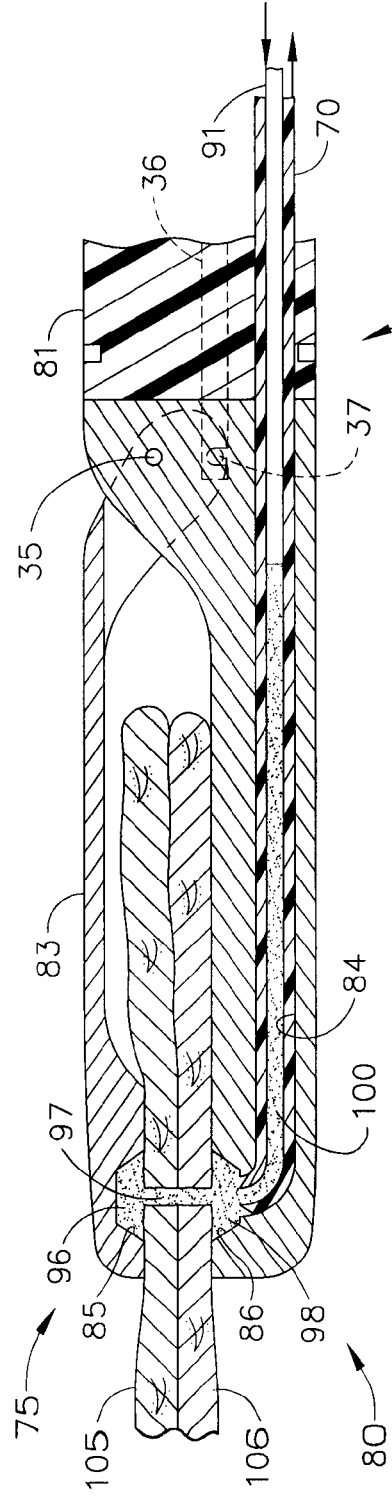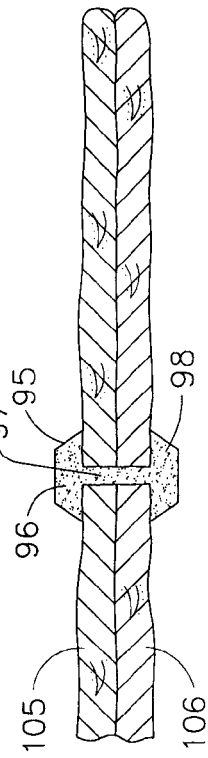

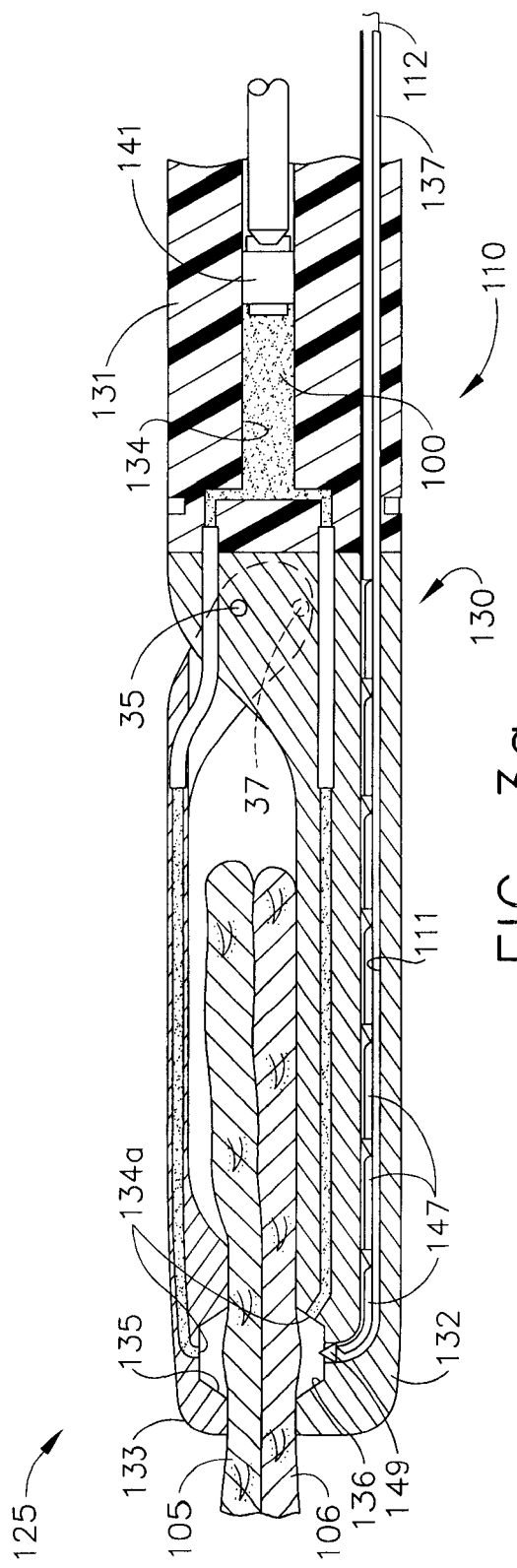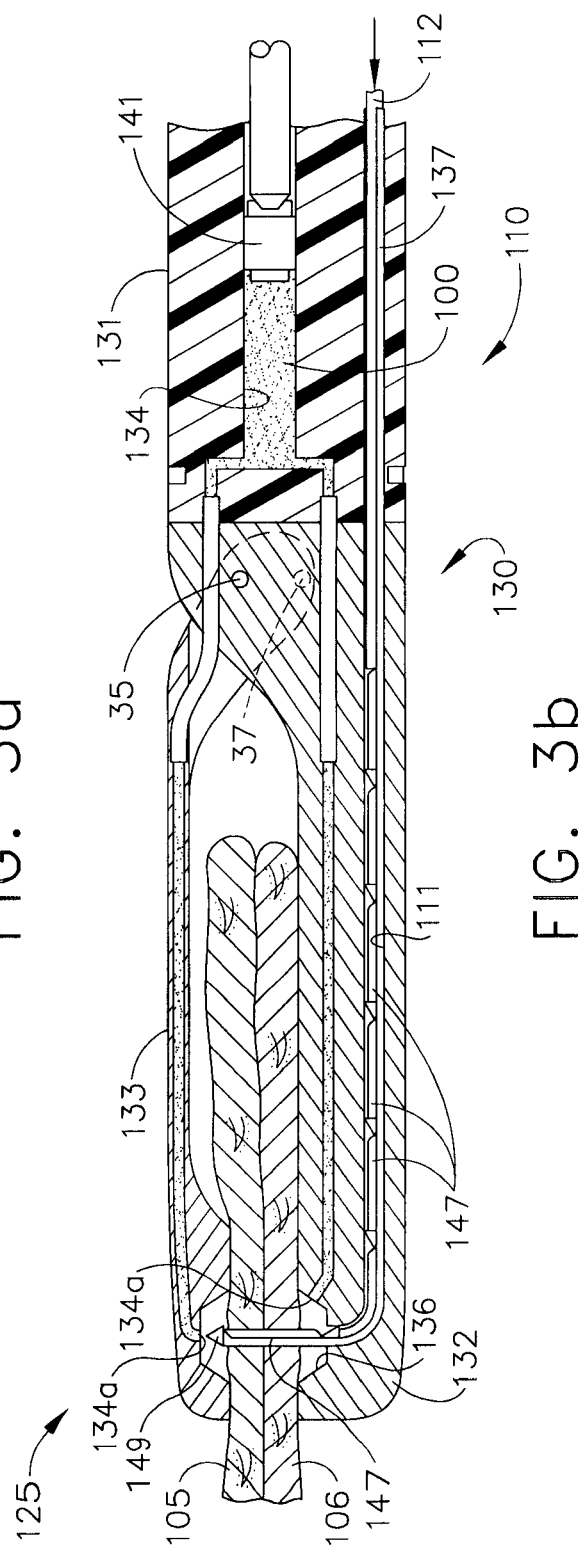

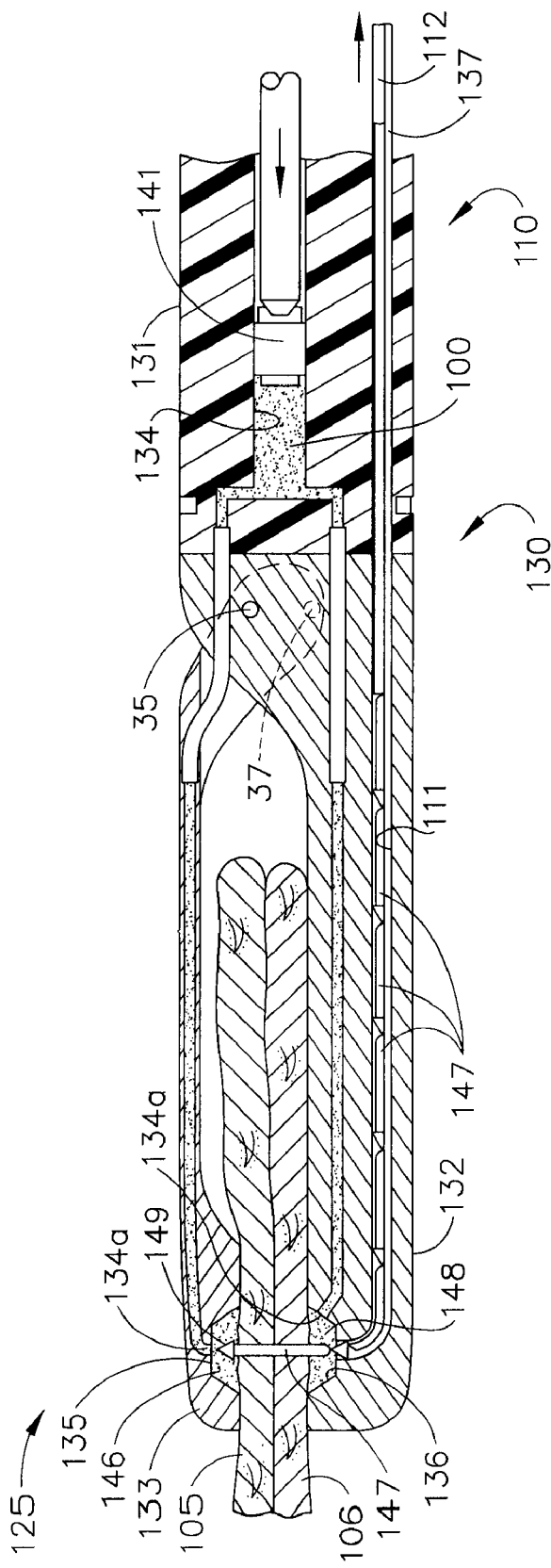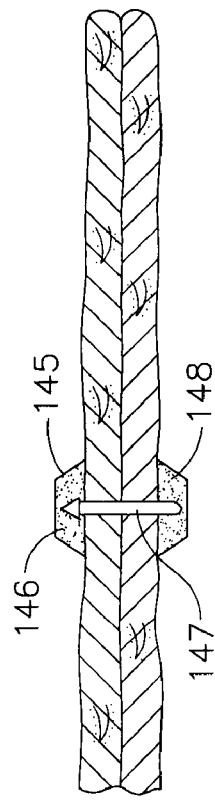
FIG. 3c
FIG. 3d

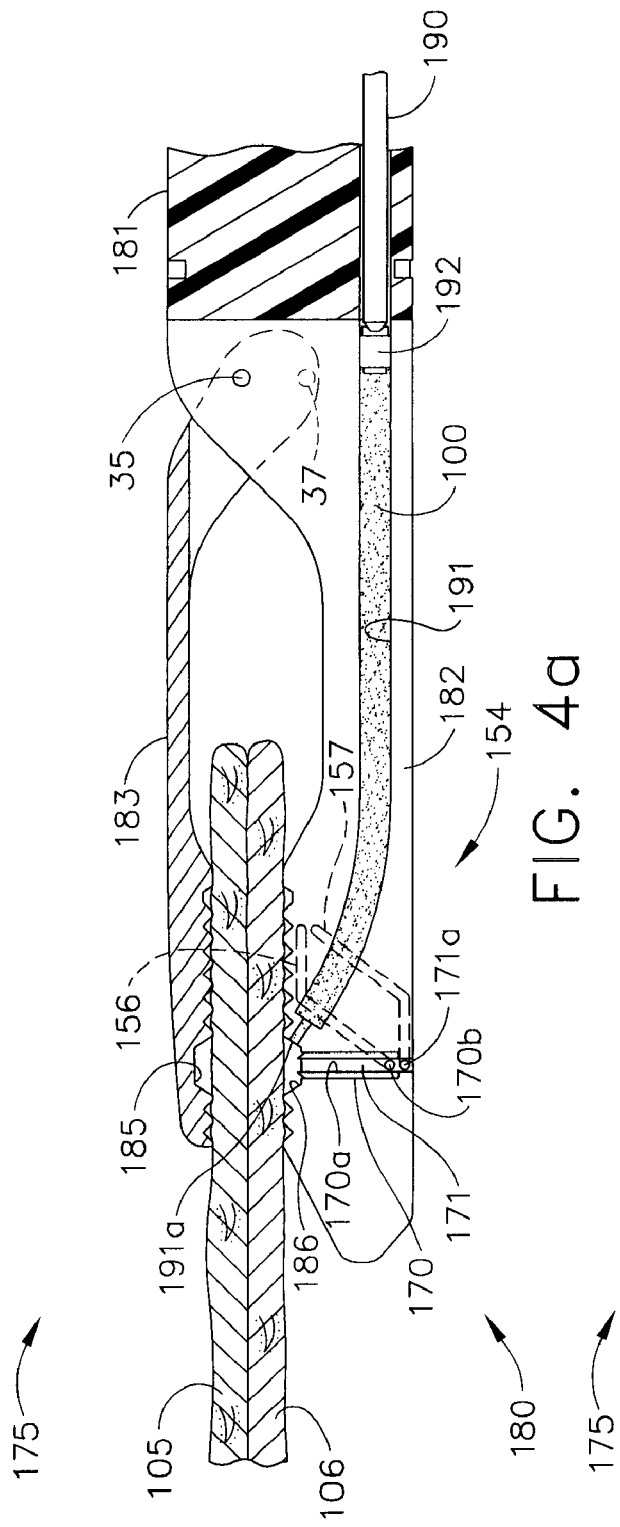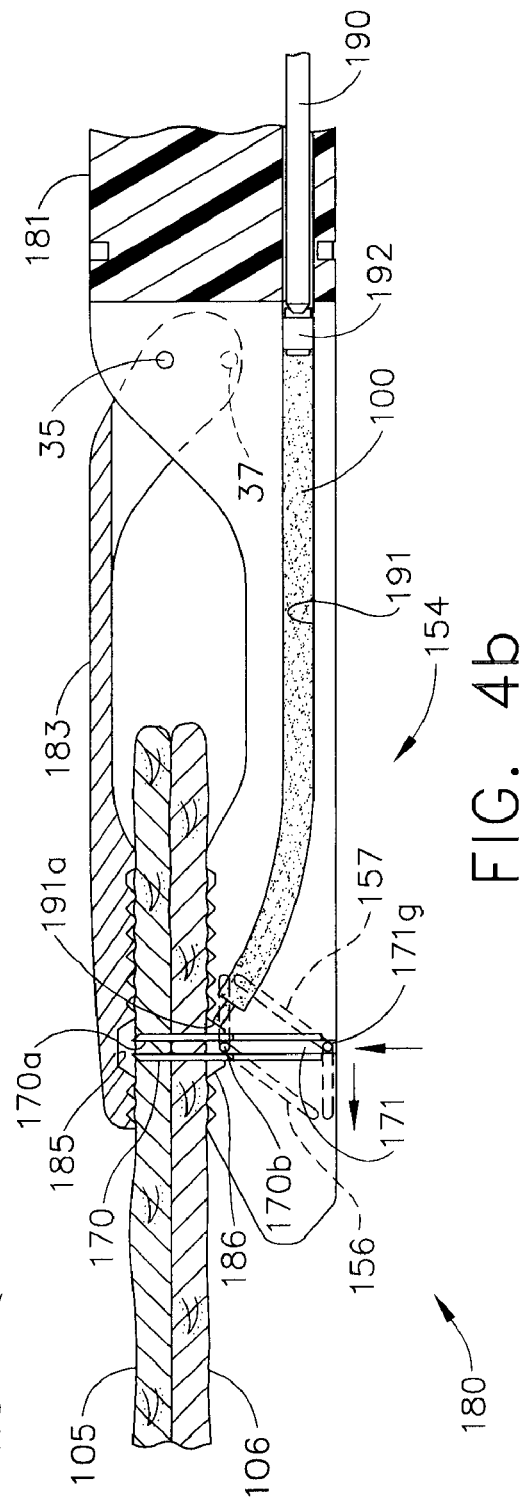

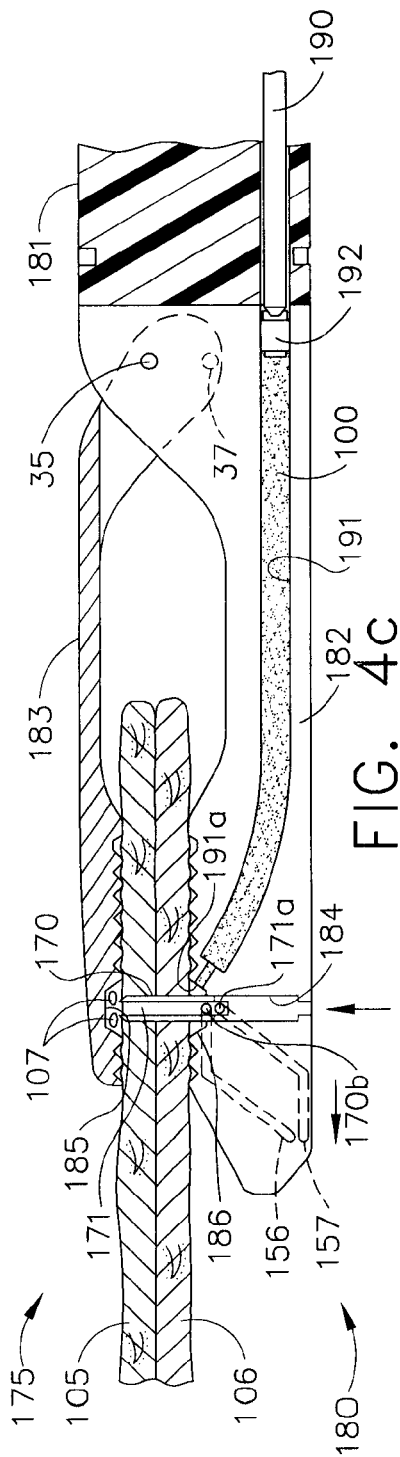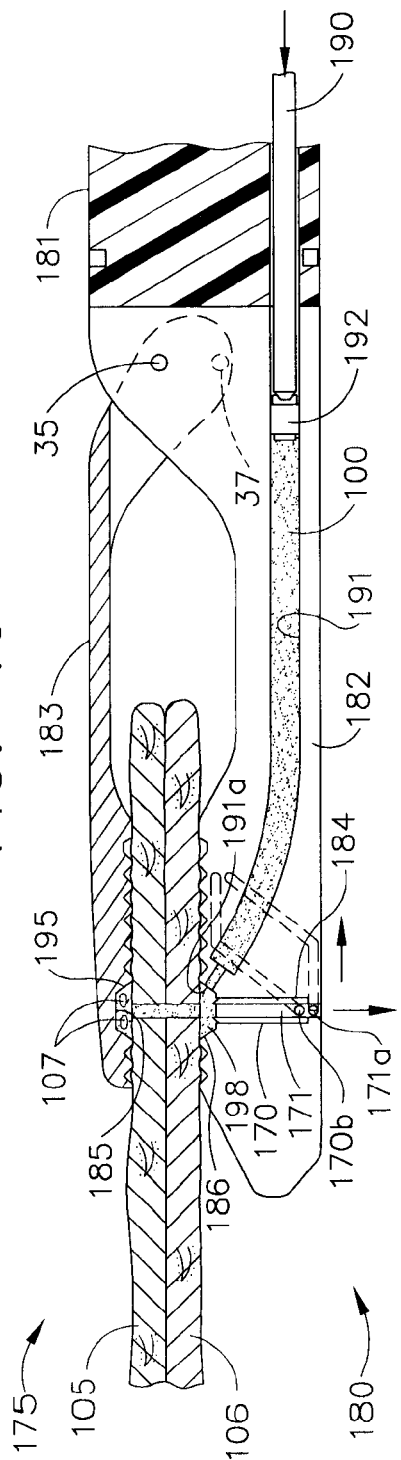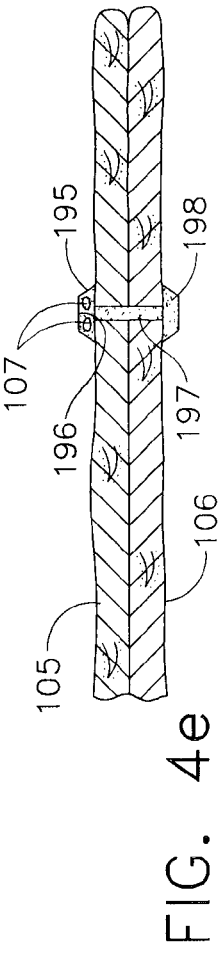

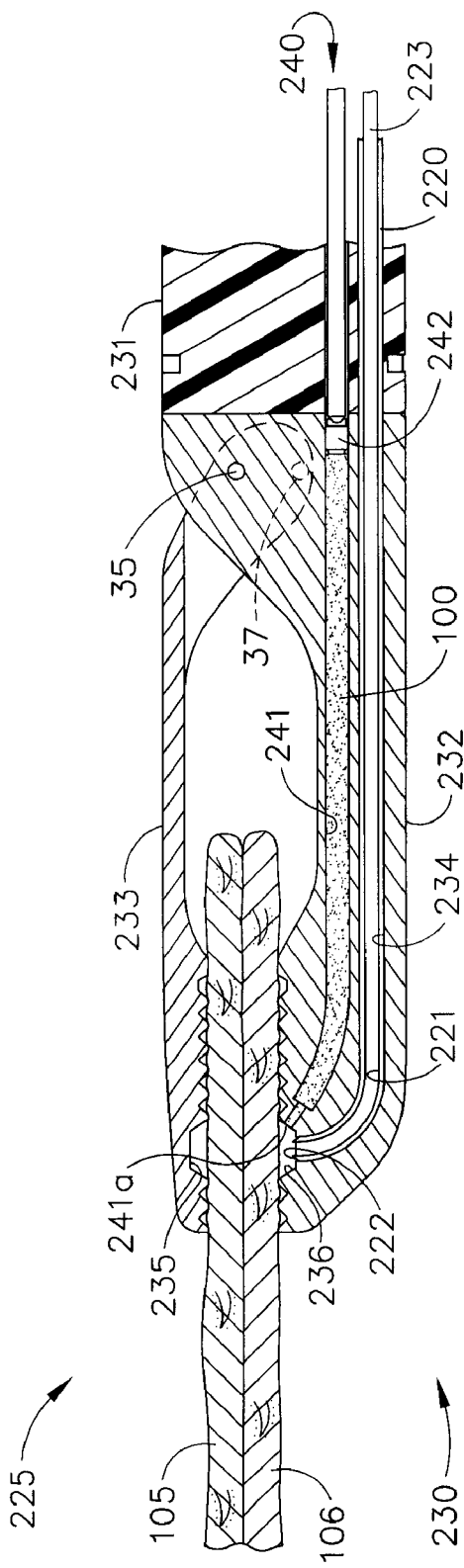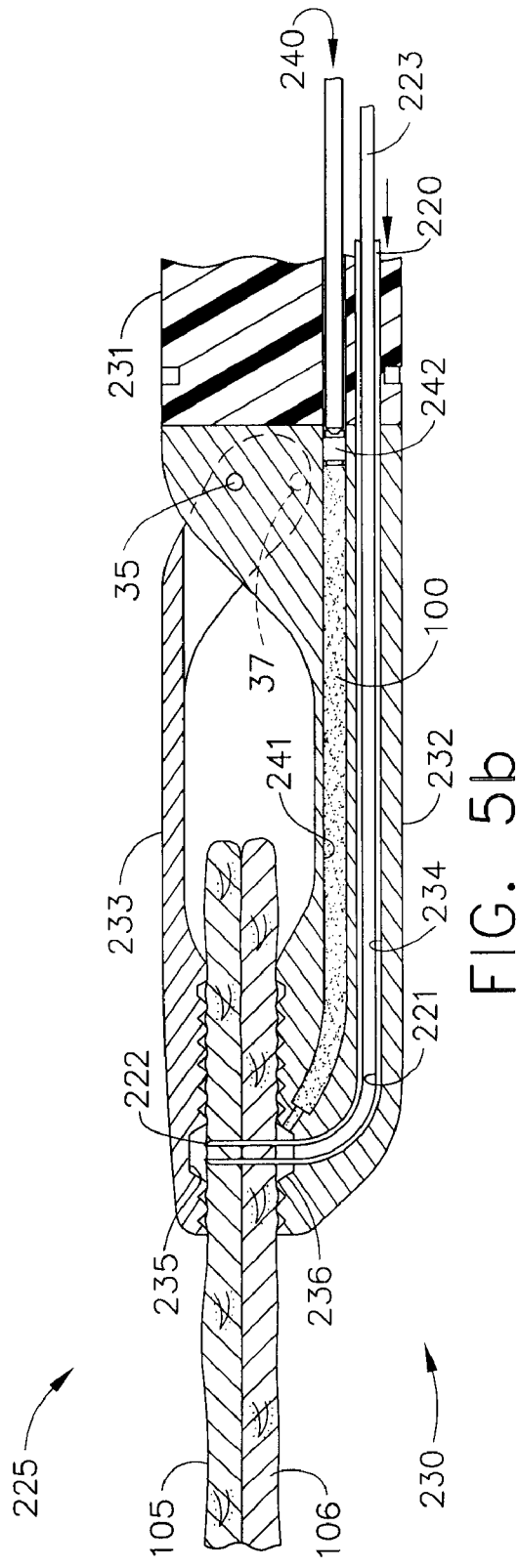
FIG. 5a
FIG. 5b

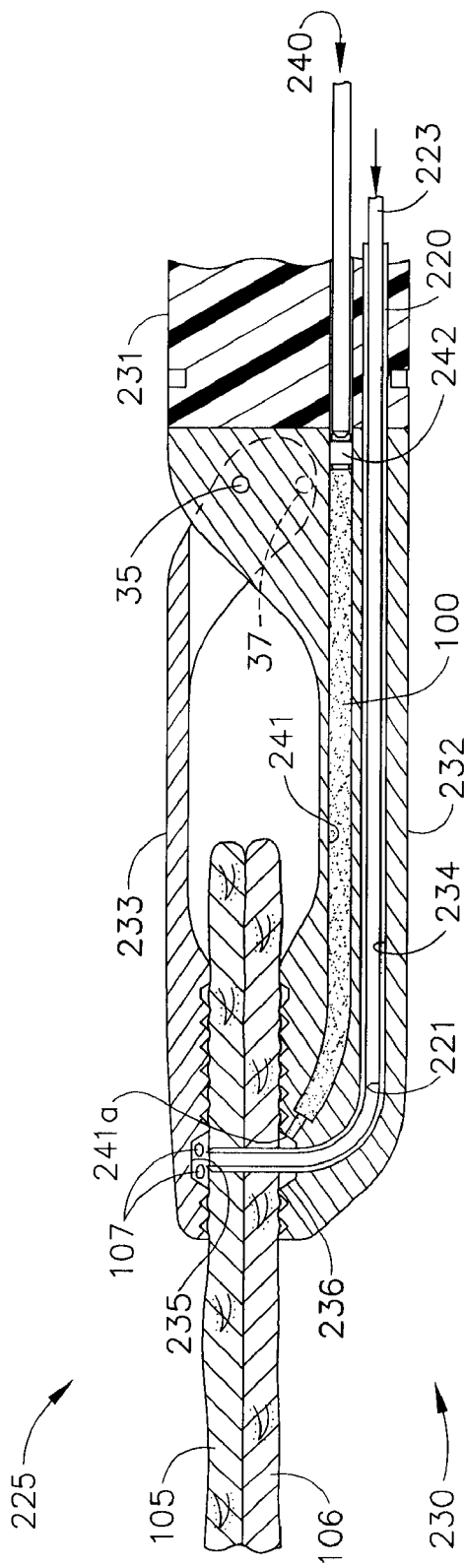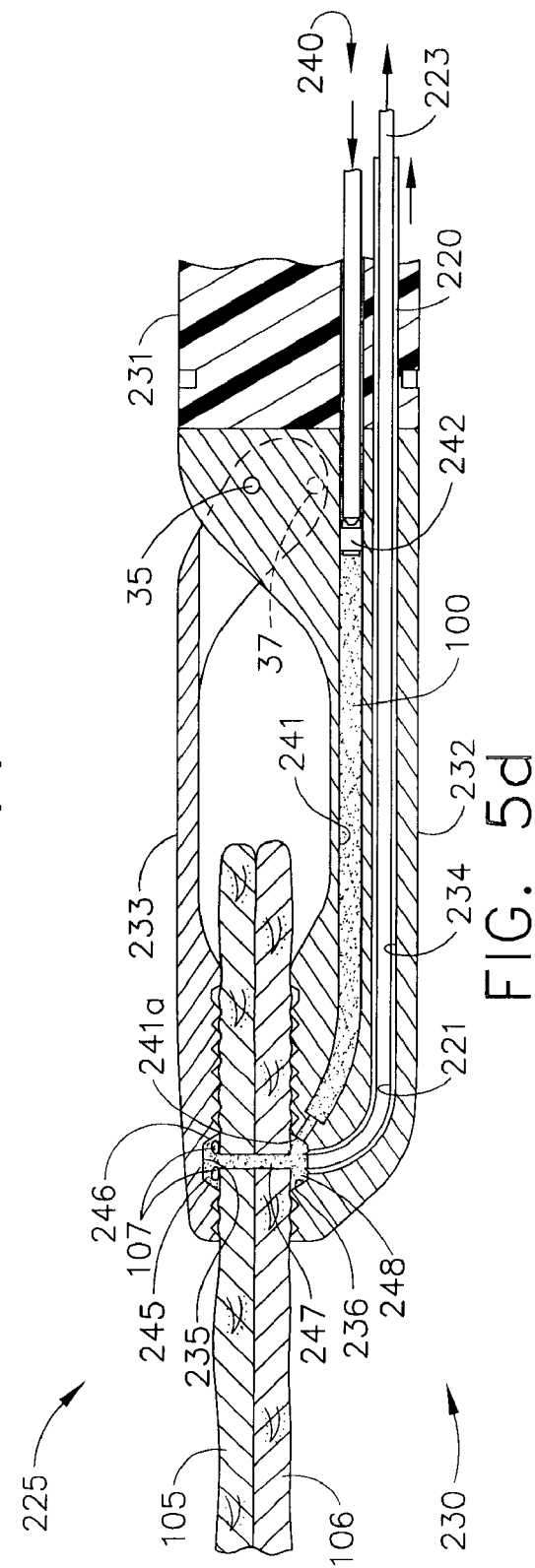
FIG. 5c
FIG. 5d

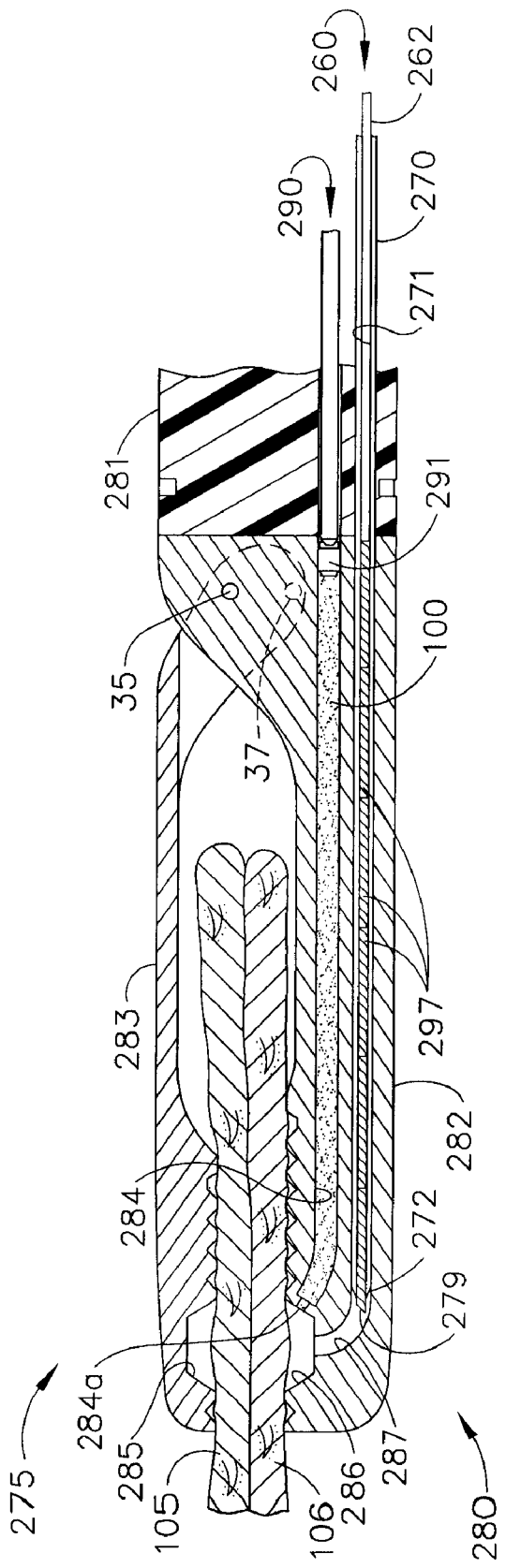
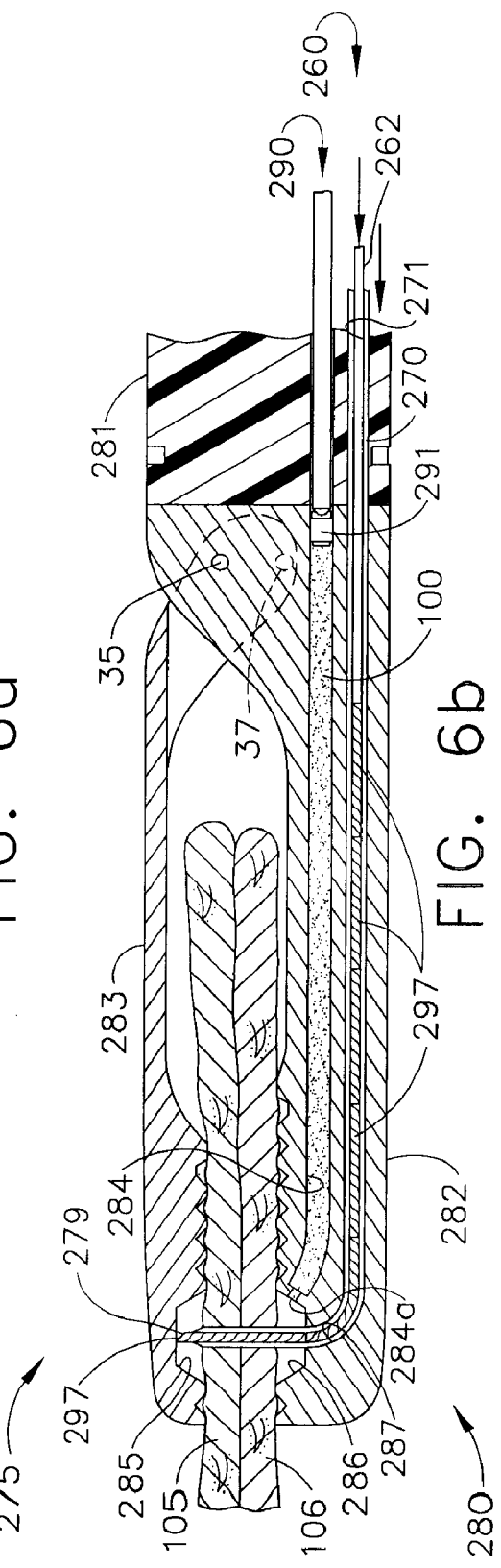

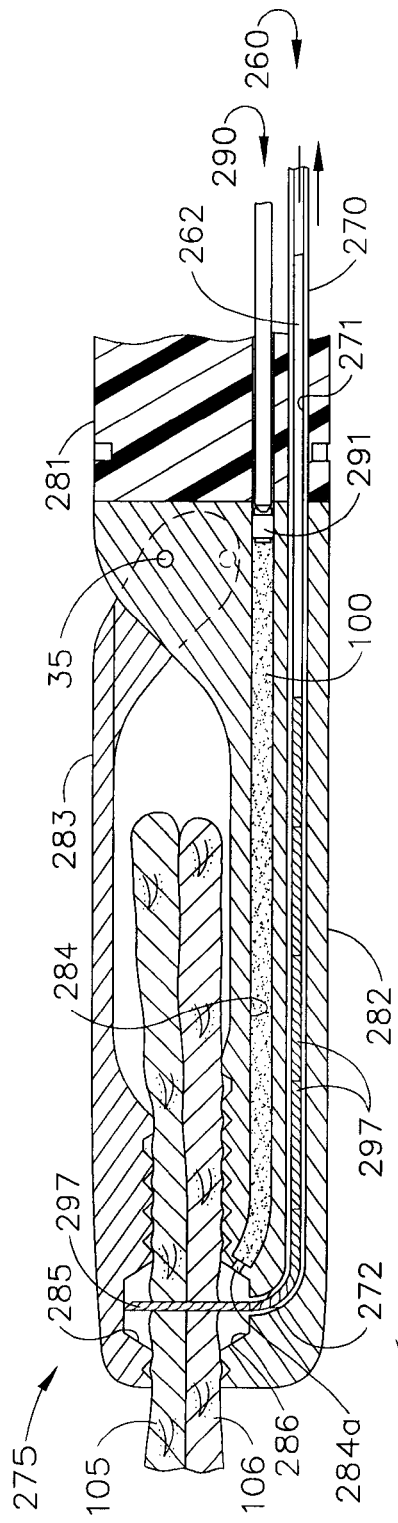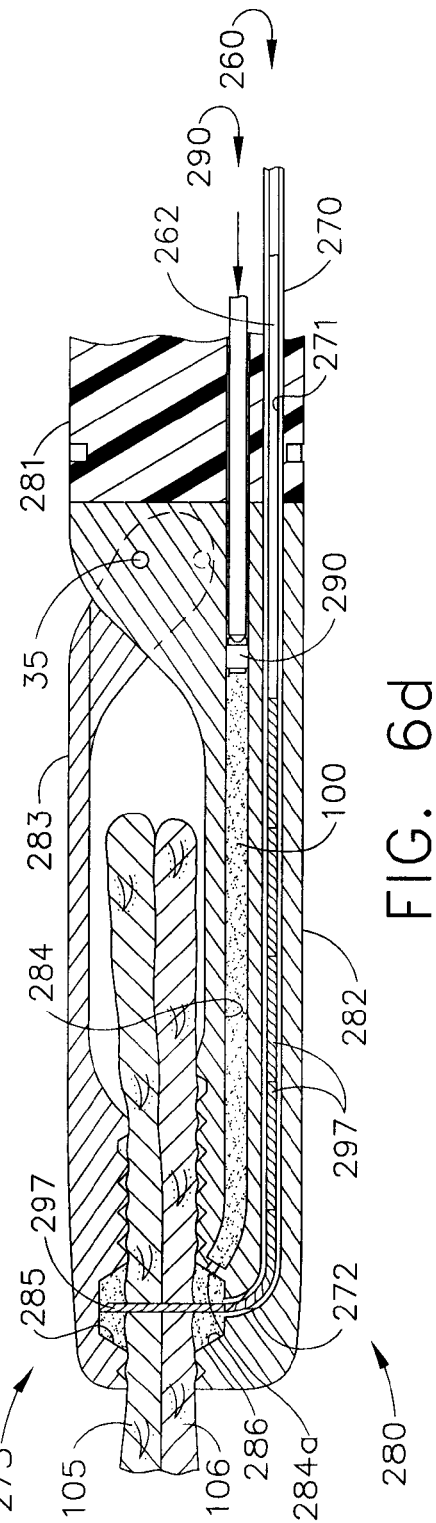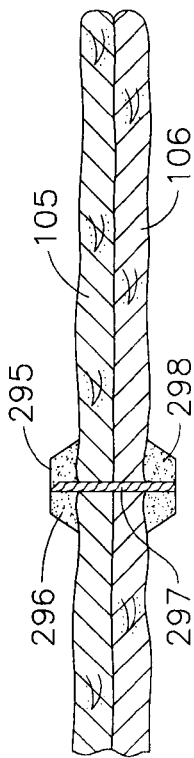

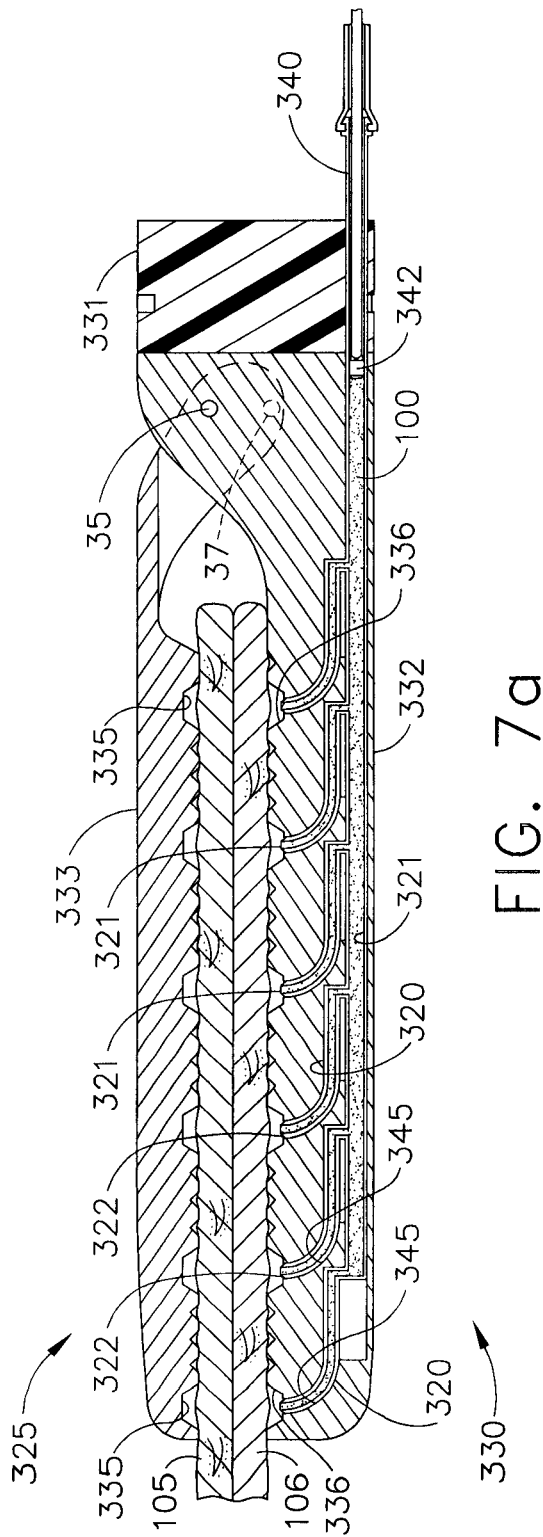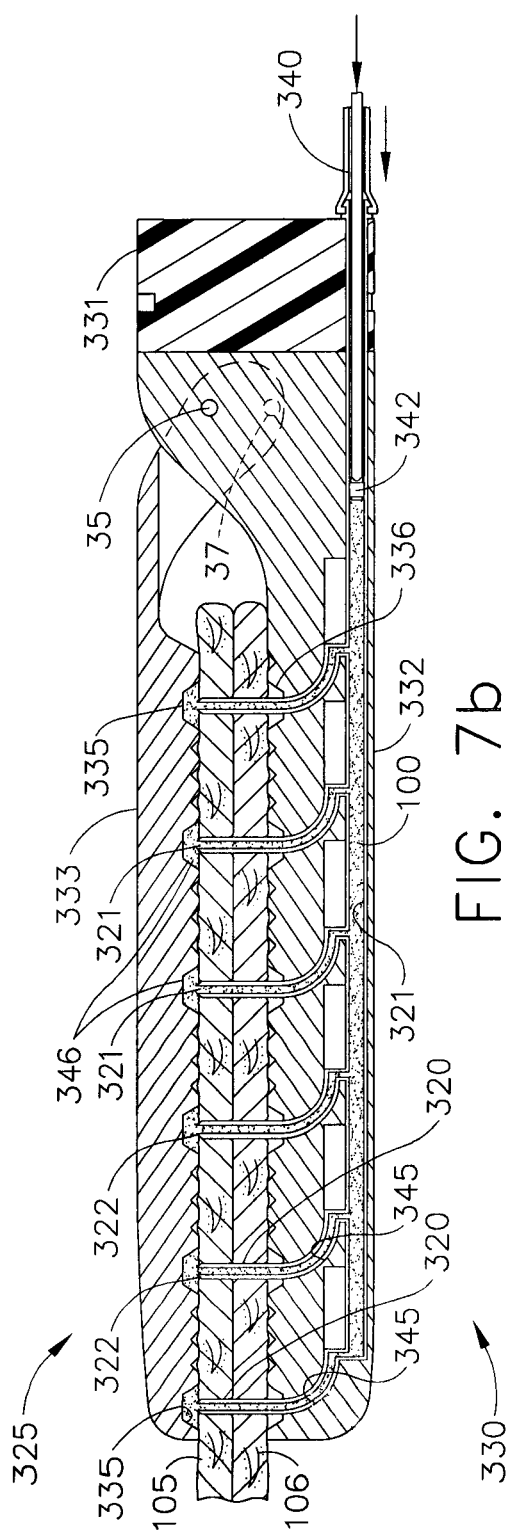

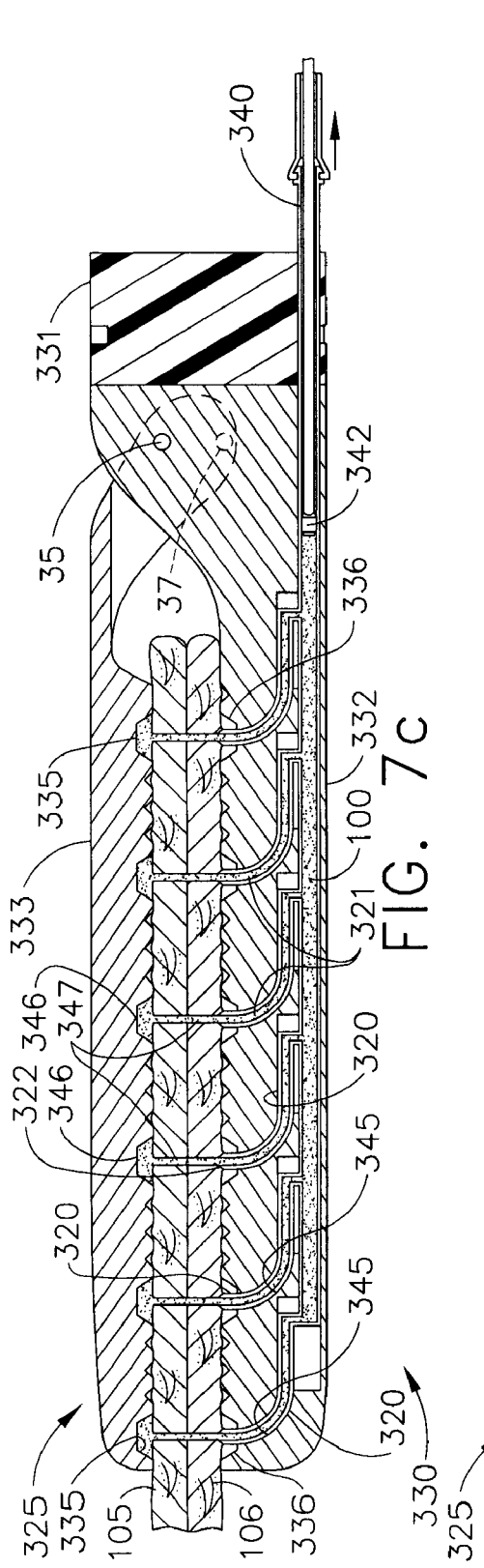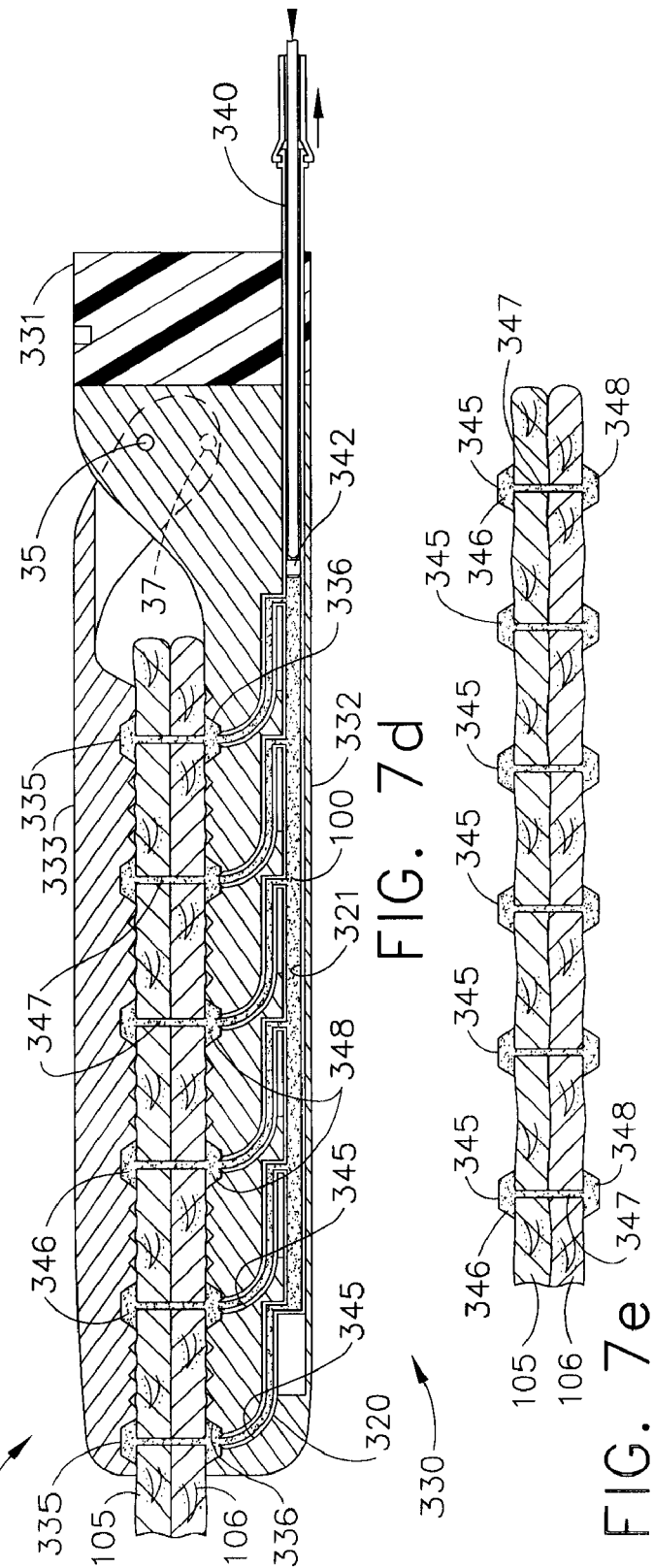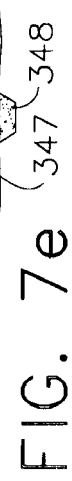

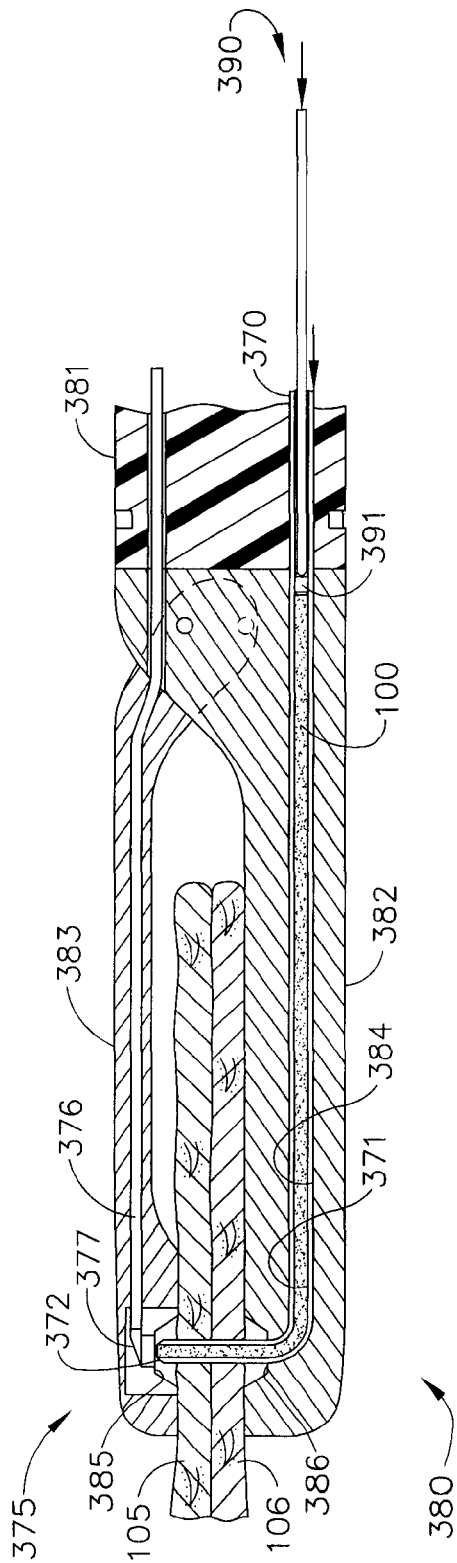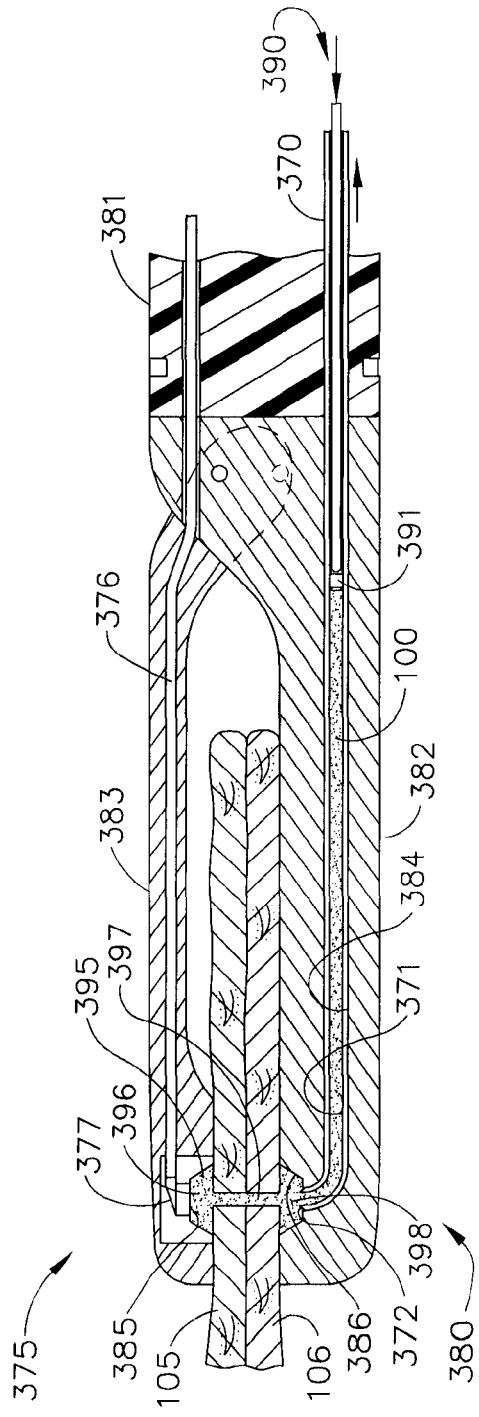

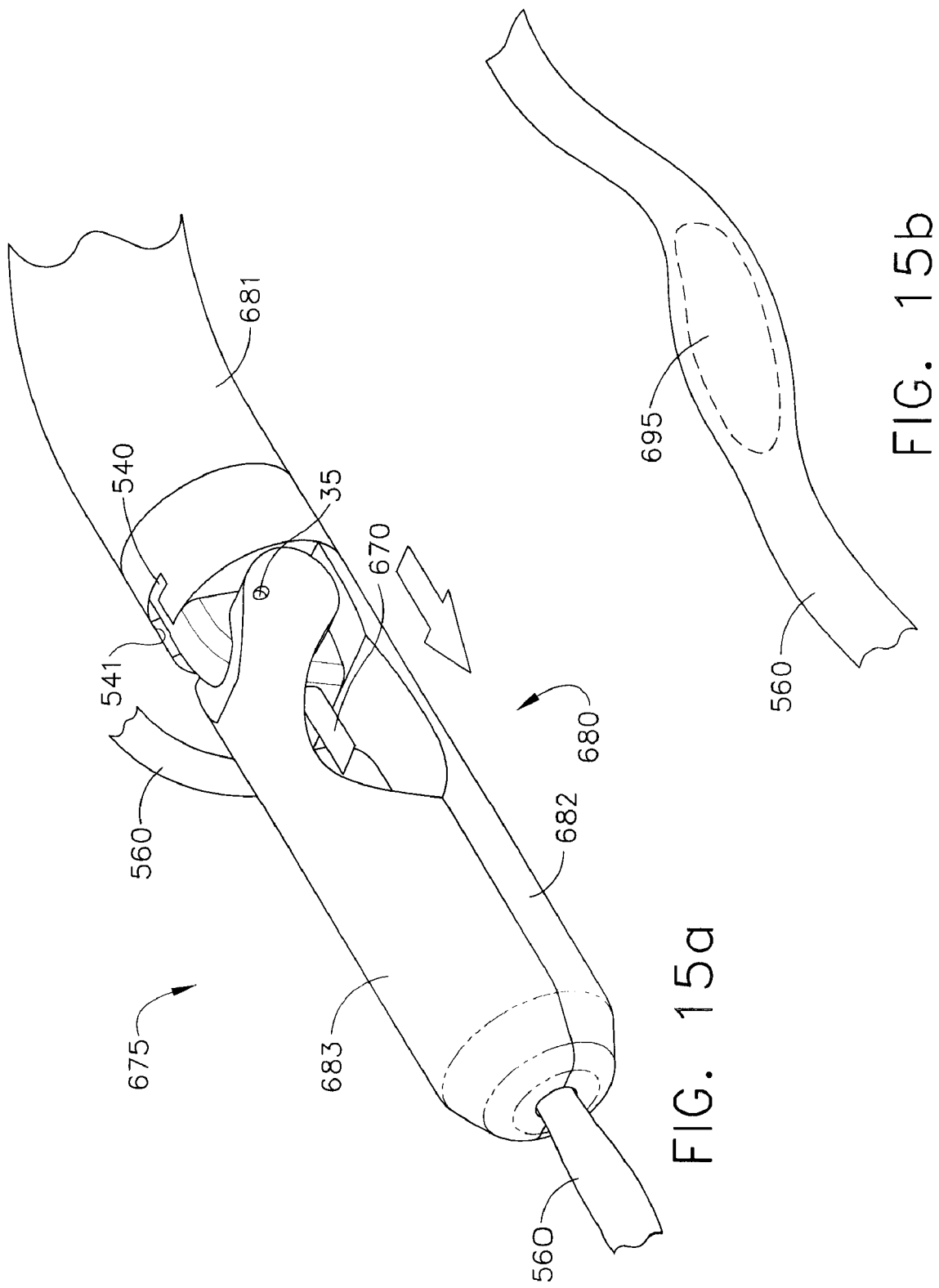

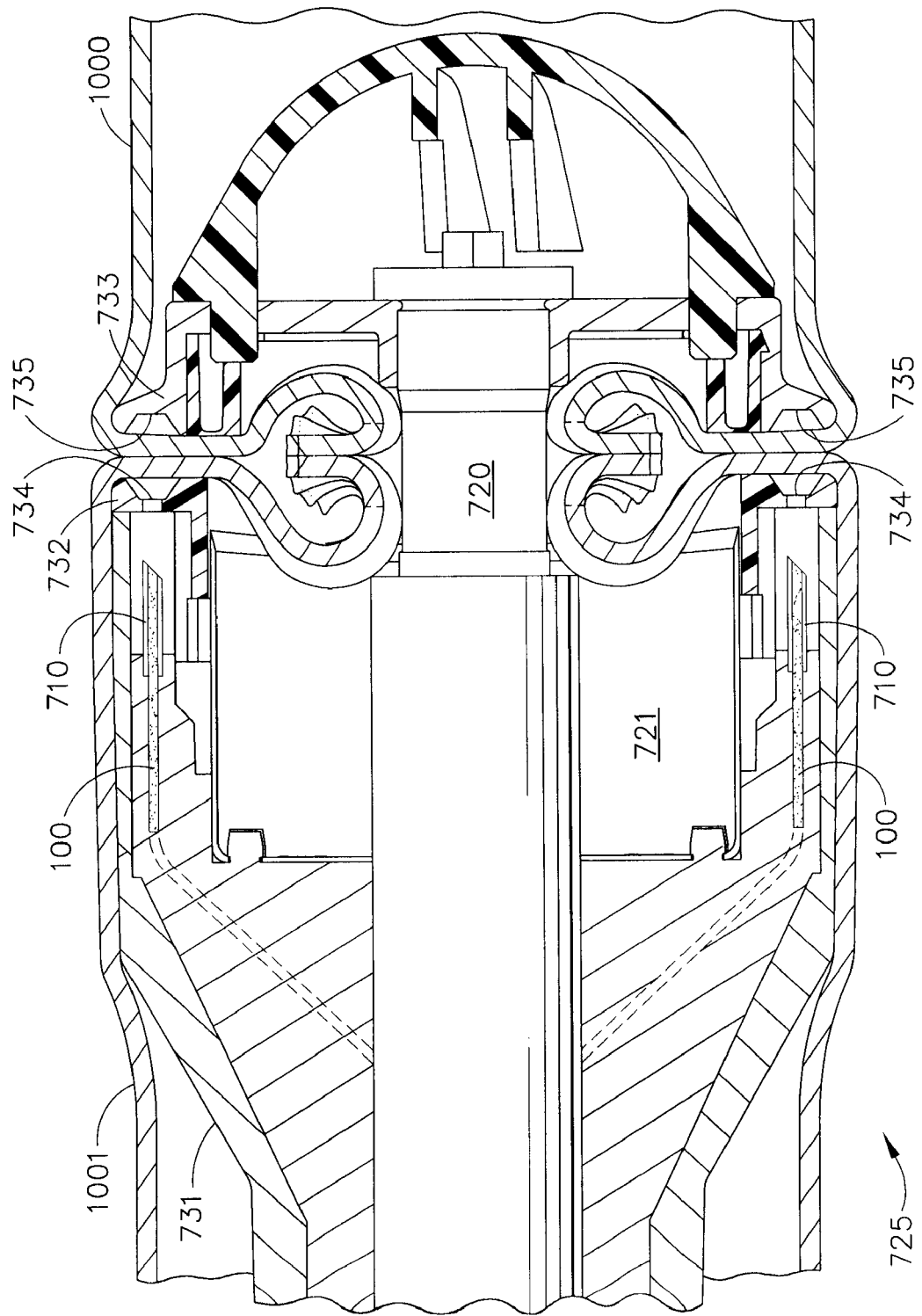

US 7,753,936 B2

FORM IN PLACE FASTENERS

FIELD OF THE INVENTION

The present invention relates, in general, to surgical fastening devices and in particular, to surgical fastening devices that can create fasteners from an adhesive.

BACKGROUND OF THE INVENTION

Adhesives and sealants have been contemplated to supplement or replace staple based transaction devices for many years. The primary challenges in accomplishing this are control of getting the adhesive into the correct location at the correct time as well as preventing it from adhering the stapler itself to the treatment site. Adhesives have proven themselves as great short term bonding/sealing mechanisms. In Europe, some surgeons prefer absorbable fasteners over non-absorbable fasteners such as staples. It would be advantageous to form or create fasteners from adhesive at the surgical site and more advantageous if the adhesive that was used to create the surgical fastener was absorbable.

One challenge in the creation of an adhesive fastener is the positioning of the adhesive into tissue and the forming of a fastener from adhesive.

Adhesives have been used topically as a short term fastener for wound repair. Closure Medical has developed a 2-octyl cyanoacrylate compound with a long carbon chain (eight carbons) that is biocompatible, has good bonding strength, and has received FDA approval for topical use. For short duration topical wound closure, the edges of the wound are brought together and at least one layer of the adhesive is applied along the surface of the wound line to form a barrier that holds the wound edges together. The cyanoacrylate adhesive also acts as a microbial barrier, keeping bacteria out and is eventually removed. Cyanoacrylate adhesives are described in United States Application 20040190975 by Goodman et al. which is herein incorporated by reference in its entirety.

Closure Medical is conducting an FDA clinical trial using a cyanoacrylate adhesive as an internal vascular tissue sealant and internal surgical adhesive. Some adhesives such as the cyanoacrylates, stick well to tissue. Additionally, the adhesives can be biocompatible, bioabsorbable, and/or flexible, inside the body.

Consequently, a significant need exists for a surgical fastening device that can use an adhesive to form one or more surgical fasteners, the one or more adhesive fasteners can fasten two portions of tissue together, can pin one or more portions of tissue together, can hold folded tissue together, can encapsulate a vascular or luminal structure, can fill a vascular or luminal structure with an adhesive fastener, and can be formed from an absorbable adhesive.

BRIEF SUMMARY OF THE INVENTION

The invention overcomes the above-noted and other deficiencies of the prior art by providing a surgical device for forming adhesive fasteners in one or more portions of tissue. The surgical device comprises a shaft and a first jaw extending from a distal end of the shaft and a second jaw extending from the distal end of the shaft. The second jaw is movable from a first position spaced away from the first jaw to a second position adjacent to the first jaw to clamp tissue therebetween. A fluid polymer adhesive is contained within the surgical device. The fluid polymer adhesive is polymerizable by exposure to an adhesive initiator. A fastener forming mechanism is provided for forming an adhesive fastener in tissue with the fluid polymer adhesive. Wherein at least a part of the adhesive fastener is formed by shaping the fluid polymer adhesive in contact with the one or more portions of tissue and then polymerizing the fluid polymer adhesive by exposing the shaped fluid polymer adhesive to the adhesive initiator.

In one aspect of the invention, a surgical device for forming fasteners within one or more portions of tissue is disclosed. The surgical device comprises a shaft having a proximal and a distal end and a fluid polymer adhesive contained within the shaft. The polymer adhesive is polymerized by exposure to an adhesive initiator. And, a fastener forming mechanism for forming an adhesive fastener in the one or more portions of tissue with the fluid polymer adhesive is provided. Wherein the fluid polymer adhesive is shaped into the adhesive fastener from a distal end of the shaft, and polymerized by exposing the shaped fluid polymer adhesive to the adhesive initiator.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1a is a cross sectional view of an adhesive fastening device clamped on tissue prior to the formation of an adhesive fastener to join the two portions of tissue together.

FIG. 1b is a cross sectional view of the adhesive fastening device of FIG. 1a showing the formation of a first adhesive fastener in the two portions of tissue.

FIG. 2a is a cross sectional view of a second adhesive fastening device clamped on two portions of tissue and having a bendable needle piercing the two portions of tissue.

FIG. 2b is the cross sectional view of the second adhesive fastening device of FIG. 2a showing an adhesive being applied from the bendable needle to form a first head of an adhesive fastener as the bendable needle retracts through the two portions of tissue clamped together.

FIG. 2c is the cross sectional view of the second adhesive fastening device of FIG. 2b showing the bendable needle just exiting the two portions of tissue and continuing to create a fastener from an adhesive.

FIG. 2d is the cross sectional view of the second adhesive fastening device of FIG. 2a showing the bendable needle fully retracted and a second head of adhesive being applied to the adhesive fastener from the bendable needle.

FIG. 2e is a cross sectional view of the adhesive fastener of FIG. 2d fully hardened in tissue to fasten two portions of tissue together.

FIG. 3a is a cross sectional view of a third adhesive fastening device clamped on two portions of tissue and having a plurality of bendable fastener shanks for piercing tissue stored in a feeder magazine, and an adhesive head forming system for forming adhesive heads on the bendable fastener shanks to secure two portions of tissue together.

FIG. 3b is a cross sectional view of the third adhesive fastening device of FIG. 3a showing a first bendable fastener shank inserted into the two portions of tissue and adhesive beginning to flow towards the first bendable fastener shank.

FIG. 3c is a cross sectional view of the third adhesive fastening device of FIG. 3b showing a first bendable fastener shank inserted into the two portions of tissue and adhesive forming a first and a second head of adhesive on the shank.

FIG. 3d is a cross sectional view of the adhesive fastener of FIG. 3c fully hardened in tissue to fasten two portions of tissue together.

FIG. 4a is a cross sectional view of a fourth adhesive fastening device clamped on two portions of tissue and having a coring system to punch out a passage through the tissue and an adhesive application system to apply adhesive through the passage to form a double headed adhesive fastener to secure the two portions of tissue together.

FIG. 4b is a cross sectional view of the fourth adhesive fastening device of FIG. 4b and showing a cam system moving distally to begin to drive a punching needle into the two clamped portions of tissue.

FIG. 4c is a cross sectional view of the fourth adhesive fastening device of FIG. 4b and showing the cam system moving distally to complete driving a punching needle into the two clamped portions of tissue.

FIG. 4d is a cross sectional view of the fourth adhesive fastening device of FIG. 4b and showing the cam system moving proximally to pull the punching needle out of the two clamped portions of tissue and the injection of an adhesive to force the cut plug out of the passage cut into tissue and to encapsulate the plug in adhesive.

FIG. 4e is a cross sectional view of the adhesive fastener of FIG. 4d fully hardened in tissue to fasten two portions of tissue together.

FIG. 5a is a cross sectional view of a fifth adhesive fastening device clamped on two portions of tissue and having a flexible needle coring system to punch out a passage through the tissue and an adhesive application system to apply adhesive through the passage to form a double headed adhesive fastener to secure the two portions of adhesive together.

FIG. 5b is a cross sectional view of the fifth adhesive fastening device of FIG. 5a and showing the flexible needle extended through the two portions of tissue to core out a plug of tissue.

FIG. 5c is a cross sectional view of the fifth adhesive fastening device of FIG. 5b and showing a flexible pusher rod pushing the core of tissue out of the coring needle.

FIG. 5d is a cross sectional view of the fifth adhesive fastening device of FIG. 5c and showing the flexible pusher rod and the coring needle retracted and the adhesive application system injecting adhesive to create a double headed fastener.

FIG. 6a is a cross sectional view of a sixth adhesive fastening device clamped on two portions of tissue and having a flexible needle coring system to punch out a passage through the tissue, a plurality of bendable fastener shanks for piercing tissue stored within in a feeder magazine in the coring needle, and an adhesive application system to apply adhesive to the shank inserted through tissue to form a double headed adhesive fastener to secure the two portions of adhesive together.

FIG. 6b is a cross sectional view of the sixth adhesive fastening device of FIG. 6a and showing the flexible needle containing the magazine of bendable fastener shanks extended through the two portions of tissue.

FIG. 6c is a cross sectional view of the sixth adhesive fastening device of FIG. 6b and showing the flexible needle retracted to leave a first bendable fastener shank inserted through the two portions of tissue.

FIG. 6d is a cross sectional view of the sixth adhesive fastening device of FIG. 6c and showing the adhesive application system injecting adhesive to create a double headed fastener about the first bendable fastener shank inserted through the two portions of tissue.

FIG. 6e is a cross sectional view of the adhesive fastener of FIG. 6d fully hardened in tissue to fasten two portions of tissue together.

FIG. 7a is a cross sectional view of a seventh adhesive fastening device clamped on two portions of tissue and having a multiple fastener flexible needle penetration system to penetrate tissue together.

FIG. 7b is a cross sectional view of the seventh adhesive fastening device of FIG. 7a and showing the flexible needle penetration system extended through the two portions of tissue.

FIG. 7c is a cross sectional view of the seventh adhesive fastening device of FIG. 7b and showing the adhesive application system injecting adhesive to create a plurality of top heads on a plurality of double headed fasteners formed from adhesive.

FIG. 7d is a cross sectional view of the seventh adhesive fastening device of FIG. 7c and showing the adhesive application system injecting additional adhesive to create a plurality of bottom heads on a plurality of double headed fasteners formed from adhesive.

FIG. 7e is a cross sectional view of the plurality of double headed adhesive fasteners of FIG. 7d fully hardened in tissue to fasten two portions of tissue together.

FIG. 8a is a cross sectional view of an eighth adhesive fastening device clamped on two portions of tissue and having a bendable needle piercing the two portions of tissue and a vacuum system.

FIG. 8b is the cross sectional view of the eighth adhesive fastening device of FIG. 8a showing the bendable needle retracts through the two portions of tissue clamped together and an adhesive being applied from the bendable needle to form a double headed adhesive fastener.

FIG. 12b is an isometric view of the rotate to attach detachable application head of the twelfth adhesive fastening device of FIG. 12a.

FIG. 15a is an isometric view of a second alternate embodiment of the twelfth surgical fastening device capable of forming an adhesive plug in a vessel.

FIG. 15b is an isometric view of a vessel having an adhesive plug formed therein.

FIG. 16b is a cross sectional view of the circular stapler of FIG. 16a clamping the portions of luminal tissue together and an adhesive injection system to place one or more circular arrays of adhesive fasteners to join the first and second portions of luminal tissue together.

DETAILED DESCRIPTION OF THE INVENTION

Figure 1C:
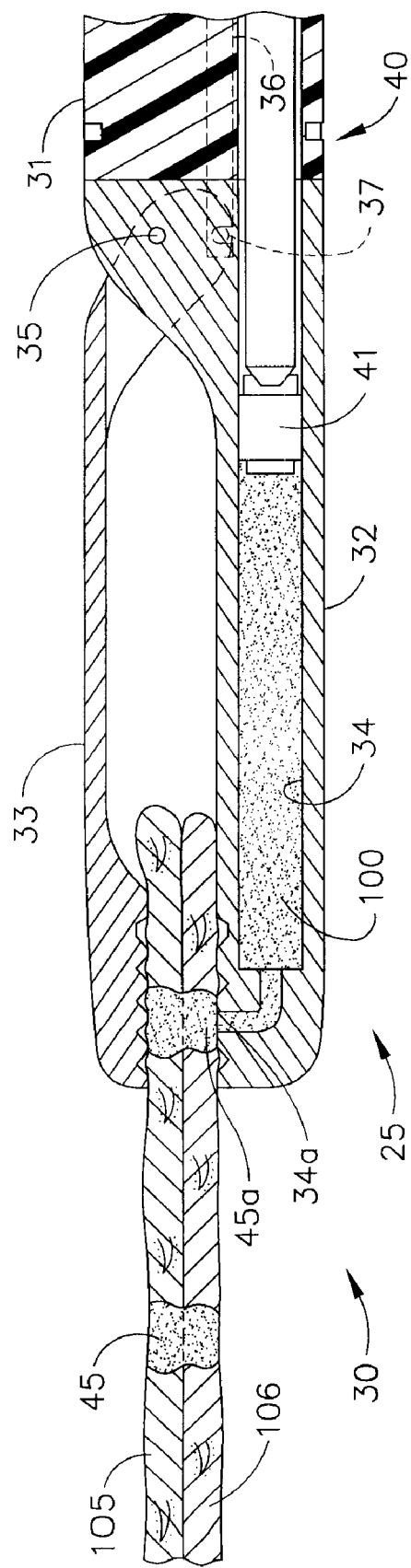
FIG. 1c is a cross sectional view of the adhesive fastening device of FIG. 1b showing the formation of a second adhesive fastener in the two portions of tissue.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Surgical fastening devices are frequently used to attach at least two portions of tissue together. Titanium staples are the predominant surgical fastener in use today and remain in the body after application. In some cases, alternate fasteners may be desired, particularly fasteners that can biodegrade over time. With new technology developments and refinements of materials, surgical fasteners using adhesives as structural components are now possible. Additionally, these adhesive fasteners can be used in other ways such as to reinforce vessels and to fasten or seal vessels.

FIG. 1a illustrates an example of an apparatus or surgical device 25 having an end effector 30 that can clamp a first portion of tissue 105 against a second portion of tissue 106 and place one or more fasteners formed entirely from a polymer adhesive 100 into tissue. The adhesive 100 can be applied to tissue in an un-polymerized state and can polymerize or set to become a fastener 100. Surgical device 25 can have an end effector 30 at a distal end of a shaft 31 with a fixed jaw 32 and a pivoting clamping jaw 33. Clamping jaw 33 can rotate about a pivot 35 from an open position to a closed position to clamp tissue. As shown, clamping jaw 33 is moved to the clamped position by pulling or moving an actuator rod 36 proximally. The proximal motion of actuator rod 36 pulls on a pin 37 of clamping jaw 33 to close the jaw 33. Distal motion of actuator rod 36 opens clamping jaw 33.

A passageway 34 can be provided to contain a polymeric adhesive 100 that could be rapidly polymerized in a number of ways such as but not limited to tissue or moisture contact. An adhesive injection system 40 may be provided with a piston 41 longitudinally movable in passageway 34 to force adhesive 100 from an orifice 34a of passageway 34 at high pressures.

Figure 1D:
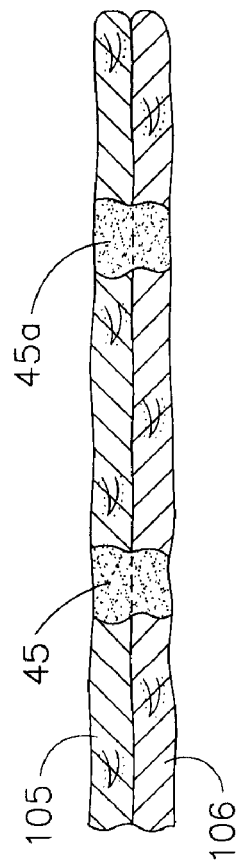
FIG. 1d is a cross sectional view of the first and second adhesive fasteners fastening two portions of tissue together.

In FIG. 1b, the piston 41 of the adhesive injection system 40 is moving distally in passageway 34 to force adhesive 100 from the orifice 35 at a high pressure to penetrate tissue to create an adhesive fastener 45 as shown. For this example, the contact of the adhesive 100 with tissue can initiate polymerization of the adhesive 100 to create a polymerized fastener 45. In FIG. 1c, a second fastener 45a is being placed into tissue with the surgical device 25. In FIG. 1d, the first portion 105 and second portion of tissue 106 are shown fastened together with adhesive fasteners 45 and 45a.

Jaw Materials for Adhesive Surgical Fastener Devices

The jaws 32, 33 of end effector 30 can be formed from materials suitable for bio-contact such as but not limited to metallic materials like stainless steel and titanium, and/or plastics like as nylons and polycarbonates and the like. Additionally, the materials of the jaws 32, 33 can be formed from materials known for their difficulty to form a glue bond such as polyethylene and polypropylene. These materials can be used with any embodiments below of the adhesive fastener forming devices.

Closure Mechanisms for Adhesive Surgical Fastener Devices

A number of alternate embodiments of adhesive fastening devices will be described below; the jaw closure mechanism of surgical device 25 using actuator rod 36 can be merely one embodiment of a closure mechanism and can be used as an exemplary closure mechanism for any of the subsequent embodiments. For figure clarity, the actuator rod 36 may be eliminated in subsequent embodiments of clamping jaws.

The Adhesive for the Fastener

One example of a polymer adhesive 100 could be a polymerizable cyanoacrylate adhesive. The adhesive 100, for example, may be but not limited to a monomeric (including prepolymeric) adhesive composition, a polymeric adhesive composition, or any other compound that can adhere to tissue and create a barrier to nutrient absorption. In embodiments, the monomer may be a 1,1-disubstituted ethylene monomer, e.g., an .alpha.-cyanoacrylate. When cross linked, the cyanoacrylate changes from a liquid to a solid adhesive. Cross linked adhesive can be a rigid or a flexible and can be non-permeable or permeable. If desired adhesive be a single part or dual part adhesive, and/or can contain additives 101. Alternately any other polymerizable adhesives 100 can be used such as a polymerizable acrylic, epoxy or silicones. Any of the exemplary adhesives 100 can be polymerized by a number of polymerization initiators such as but not limited to polymerization initiating compounds, light, Ultraviolet light, moisture, and tissue contact. For example, moisture and ultraviolet curing grades of adhesive 100 can include cyanoacrylates, acrylics, epoxys and silicones for forming adhesive fasteners.

Additives to the Adhesive

Examples of additives 101 can include, but are not limited to: adhesive initiators 102, release agents 103, image enhancing agents, necrosing agents, sclerosing agents, coagulants, theraputic agents, medicaments, analeptic agents, anesthesia agents, antidiuretic agents, analgesic agents, antiseptic agents, antispasmodic agents, cardiac agents, depressant agents, diuretic agents, hemostatic agents, hormonal agents, sedative agents, stimulant agents, vascular agents, time release agents, absorbable materials (see below, colorants, plasticizing agents, bulking agents, tamponade materials, thixotropic agents, antibacterial agents, buffers, catalysts, fillers, micro particles, thickeners, solvents, drugs, medicaments, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes.

Adhesive Initiators

Polymerization of the adhesive 100 can occur from tissue contact, moisture, spraying with saline or by use of an adhesive initiator 102. Adhesive initiators 102 are for polymerization and/or cross-linking of a polymerizable monomer. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25.degree C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

To one skilled in the art, other compounds such as additives 101, adhesive initiators 102 and release agents 103 can be used in combination with any surgical device that can create all or part of an entire adhesive fastener.

Additionally, other compounds 101, 102, 103 or combinations thereof can be provided in or on or about an end effector of an adhesive fastener forming device such as but not limited to the example end effector 30. These additives 101 can be combined with the materials of the end effector elements, supplied as coatings, or any other way of securing the additives 101 to end effector elements. For example, suitable adhesive initiators 102 may be placed on end effector elements such as release agents 103 such as but not limited to polytetraflouroethylene compounds, silicone compounds and the like to prevent sticking of the adhesive 100 to end effector 30 parts thereof, or can contain compounds such as adhesive initiators 102 to induce adhesive polymerization of the adhesive 100 by contact with end effector elements.

Other suitable adhesives 100, additives 101, adhesive initiators 102, release agents 103, may be found in United States Application 20040190975 by Goodman et al. which is herein incorporated by reference in its entirety.

A Second Surgical Adhesive Fastening Device

FIG. 2a illustrates an example of a second apparatus or adhesive fastening device 75 having an end effector 80 that can clamp the first portion of tissue 105 against a second portion of tissue 106 and place one or more dual headed adhesive fasteners 95 into tissue. The dual headed fastener 95 is best shown in FIG. 2e and can comprise a first head 96, an adhesive shank 97 and a second head 98 formed from adhesive 100 with the fastening device 75. The fastening device 75 can have a flexible needle 70 formed from a bendable materials such as but not limited to nitinol and polypropelene that is used to penetrate tissue in the creation of the dual headed fastener 95 from adhesive 100.

Surgical device 75 may have an end effector 80 at a distal end of a shaft 81. The end effector 80 may have a movable jaw 83 and a fixed jaw 82 for clamping tissue therebetween and a first pocket 85 within movable jaw 83 and a second pocket 86 within fixed jaw 82 for forming first and second adhesive heads 96, 98 respectively therein. A passageway 84 is located in fixed jaw 82 and contains the flexible needle 70 movable therein. Flexible needle 70 has a sharp edge 72 for piercing and cutting tissue and a bore 71 containing a polymeric adhesive 100 that can be injected therefrom and rapidly polymerized by tissue contact into the adhesive fastener 95. An adhesive injection system 90 may have a piston rod 91 longitudinally movable in bore 71 to force adhesive 100 from bore 71 about the tissue 105, 106.

For this and any further embodiment of a surgical fastener device described below, a coating such as polytetraflouroethylene (PTFE) could be placed within first head forming first pocket 85 and second pocket 86 to reduce unwanted adhesions between the fastener 95 and jaws 82, 83 as well as an adhesive initiator 102 to induce polymerization of the adhesive 100.

In FIG. 2a, the jaws 82, 83 are clamped on tissue 105, 106 and both the flexible needle 70 and piston rod 91 may be shown moving distally in passageway 84 to pierce the tissue 105, 106 with a sharp edge 72. The flexible needle 70 and piston rod 91 can move at the same rate in passageway 84 to prevent tissue entry into the flexible needle 70.

In FIG. 2b, the flexible needle 70 and piston rod 91 may be shown moving proximally in passageway 84 and through tissue 105, 106, and adhesive 100 is being injected into first pocket 85 to form a first head 96 of the adhesive fastener 95.

In FIG. 2c, the flexible needle 70 and piston rod 91 can move proximally in passageway 84 to withdraw flexible needle 70 from the first and second portions of tissue 105, 106 after having formed the shank 97 through tissue 105, 106 and attached to the first head 96 of the adhesive fastener 95. In FIG. 2d, the flexible needle 70 and piston rod 91 can move to a fully retracted position to form a second head 97 attached to the shank 97 of the adhesive fastener 95. For this example, the adhesive 100 of first head 96, the shank 97 and the second head 98 of adhesive fastener 95 are polymerizing from tissue contact as well as contact with the adhesive initiator 102 within first pocket 85 and second pocket 86.

A Third Adhesive Fastening Device

FIG. 3a is a cross sectional view of a third adhesive fastening device 125 having an end effector 130 clamped on two portions of tissue 105, 106 for the creation of a dual headed surgical fastener 145 having a first adhesive head 146, a flexible shank 147 of a non-adhesive material such as but not limited to titanium, stainless steel, nitinol, biocompatible plastics, and the like, and a second adhesive head 148 formed on the opposite end of the flexible shank 147.

In FIG. 3a, surgical device 125 has an end effector 130 at a distal end of a shaft 131. The end effector 130 can have a movable jaw 133 and a fixed jaw 132 for clamping tissue therebetween and a first pocket 135 within movable jaw 132 and a second pocket 136 within fixed jaw 132 for forming first and second adhesive heads 146, 148 respectively therein. A feeder mechanism 110 could have a magazine passage 111 containing a plurality of flexible shanks 147 and a longitudinally movable shank pusher 112 for pushing the stack of flexible shanks 147 therethrough. Each of the flexible shanks 147 can have a point 149 for piercing tissue. An adhesive injection system 140 may have a piston 141 longitudinally movable in a bifurcated passageway 134 to force adhesive 100 from a pair of orifices 134a of bifurcated passageway 134.

In FIG. 3b, a first flexible shank 147 could be shown pushed through the two portions of tissue 105, 106 by distal movement of movable shank pusher 112. A flexible guide trough 137 can be provided to bend at right angles to support and guide the flexible shanks 147 as they pierce tissue In FIG. 3c, the piston 141 can be shown moving distally in passageway 134 to push adhesive 100 from the pair of orifices 134a of bifurcated passageway 134. The adhesive 100 may sequentially or simultaneously form the first adhesive head 146 within the first pocket 136 and the second adhesive head 148 within the second pocket 137 and about the ends of the first flexible shank 147.

FIG. 3d shows a fully polymerized fastener 145 fastening two portions of tissue 105, 106 together, the fastener 145 comprising a first adhesive head 146 and the second adhesive head 148 formed on the shank 147.

A Fourth Surgical Adhesive Fastener Device

FIG. 4a is a cross sectional view of a fourth adhesive fastening device 175 having an end effector 180 clamped on two portions of tissue 105, 106 for the creation of a dual headed adhesive fastener 195 having a first adhesive head 196, an adhesive shank 197, and a second adhesive head 198 formed on the opposite end of the shank 197.

The surgical fastening device 175 may have a movable jaw 183 and a fixed jaw 182 for clamping tissue therebetween and a first pocket 185 within moveable jaw 182 and a second pocket 186 within fixed jaw 182 for forming first and second adhesive heads 196, 198 respectively therein. Cross hatching has been removed from fixed jaw 182 for clarity. A piercing system 154 can be provided having a hollow piercing needle 170 that reciprocates vertically within a needle passage 184 (FIG. 4c) within a fixed jaw 182. The piercing needle 170 has a hollow 170a and can penetrate and hold a tissue remnant 107 within. A tissue pusher 171 can reciprocate independently within the hollow 170a of piercing needle 170 to push tissue remnants 107 from the hollow 170a and into the first pocket 185 within moveable jaw 182. When the fastener 195 is formed, the adhesive 100 encapsulates the tissue portions 107 within the polymerized adhesive 100 (FIGS. 4d and 4e).

In FIG. 4a, the coring needle 170 resides in the passage 184 of fixed jaw 182, and tissue pusher 171 resides within the hollow 170a of the coring needle 170. The piercing system 154 further includes a longitudinally movable cam plate 155 (not shown) within fixed jaw 182 and located behind coring needle 170. Cam plate 155 can have a first cam path 156 for the reception of a needle pin 170b therein and a second cam path 157 for the reception of a tissue pusher pin 171a therein. Longitudinal reciprocation of cam plate 155 lifts and retracts coring needle 170 and tissue pusher 171 as will be described below. An adhesive application system 190 may have a bore 191 filled with adhesive 100 and an adhesive piston rod 192 longitudinally movable in the bore 191 to force adhesive 100 from bore 191, from an orifice 191a, and into second pocket 186.

FIG. 4b could show cam plate 155 moving distally to lift coring needle 170 into tissue 105, 106 via engagement of needle pin 170b with a ramp of first cam path 156. The tissue pusher 171 remains in position as tissue pusher pin 171a travels along a flat portion of second cam path 157. Tissue remnants 107 can reside in hollow 170a of the coring needle 170.

FIG. 4c can show the cam plate 155 at the distal most portion of longitudinal travel. A flat portion of first cam path 156 engage with needle pin 170b to hold coring needle 170 in the uppermost position extending from passageway 184. A ramped portion of second cam path 157 engaging with the tissue pusher pin 171a may raise tissue pusher 171 vertically out of passageway 184 and into hollow 170a of the coring needle 170 to push tissue remnants 107 from hollow 170a and into the first pocket 185 within moveable jaw 182.

FIG. 4d can show the cam plate 155 moved proximally to draw tissue coring needle 170 and pusher 171 back down into the passageway 184 to the position of FIG. 4a. The adhesive piston rod 192 may be shown moved longitudinally in the bore 191 to force adhesive 100 from bore 191, from an orifice 191a, into second pocket 186, through the passageway cut by coring needle 170 in tissue 105, 106 and into the first pocket 185 to create adhesive fastener 195. The first adhesive head 196 of adhesive fastener 195 can contain encapsulated tissue remnants tissue remnants 107.

FIG. 4e may show a fully polymerized fastener 195 fastening two portions of tissue 105, 106 together, the fastener 145 comprising a first adhesive head 196 enveloping tissue remnants 107, an adhesive shank 197, and the second adhesive head 198.

A Fifth Surgical Adhesive Fastener Device

FIG. 5a is a cross sectional view of a fifth adhesive fastening device 225 having an end effector 230 clamped on two portions of tissue 105, 106 for the creation of a dual headed surgical fastener 245 having a first adhesive head 246, an adhesive shank 247, and a second adhesive head 248 formed on the opposite end of the shank 247. The surgical device 225 can have a flexible needle 220 that is used to penetrate tissue in the creation of the dual headed fastener 245 from adhesive 100.

Surgical device 225 may have an end effector 230 at a distal end of a shaft 231. The end effector 230 can have a fixed jaw 232 and a movable clamping jaw 233 with a first pocket 235 within moveable jaw 232 and a second pocket 236 within fixed jaw 232 for forming first and second adhesive heads 246, 248 respectively therein. A passageway 234 is located in fixed jaw 232 and contains a flexible needle 220 movable therein and a bend to direct flexible needle 220 towards fixed jaw 232. Flexible needle 220 has a sharp edge 222 for piercing and cutting tissue and a bore 221. A longitudinally movable bendable tissue plunger 223 is located in bore 221 for tissue ejection. An adhesive application system 240 may be provided and have a bore 241 filled with adhesive 100 and an adhesive piston rod 242 longitudinally movable in the bore 241 to force adhesive 100 from bore 241, from an orifice 241a, and into second pocket 236.

FIG. 5b can show the flexible needle 70 moved distally to pierce through the tissue portions 105, 106 and contain tissue remnants 107 within the bore 221.

In FIG. 5c the flexible tissue plunger 223 can move distally to eject tissue remnants 107 from the bore 221 in flexible needle 220 and into first pocket 235.

In FIG. 5d, both the flexible needle 70 and the flexible tissue plunger 223 have been withdrawn from tissue portions 105, 106 and from second pocket 236 within fixed jaw 232. Adhesive 100 has been injected from orifice 241a of bore 241 by distal movement of the adhesive piston rod 242 longitudinally movable in the bore 241 to force adhesive 100 therefrom. The adhesive is curing and the jaws will open next to release tissue portions 105, 106 held together with a polymerized dual headed adhesive fastener 245.

A Sixth Surgical Adhesive Fastener Device

FIG. 6a is a cross sectional view of a sixth surgical fastening device 275 having an end effector 280 clamped on two portions of tissue 105, 106 for the creation of a dual headed surgical fastener 295 having a first adhesive head 296, a flexible shank 297 of a non-adhesive material such as but not limited to titanium, stainless steel, nitinol, biocompatible plastics, and the like, and a second adhesive head 298 formed on the opposite end of the flexible shank 297. The surgical device 275 can have a flexible needle 270 movable within a passageway 287, and can be used to penetrate tissue in the creation of the dual headed fastener 295 from adhesive 100 and shank 297.

In FIG. 6a, surgical device 275 has an end effector 280 at a distal end of a shaft 281. The end effector 280 may have a movable jaw 283 and a fixed jaw 282 for clamping tissue therebetween and a first pocket 285 within movable jaw 282 and a second pocket 286 within fixed jaw 282 for forming first and second adhesive heads 296, 298 respectively therein. A feeder mechanism 260 can be provided to feed a magazine of flexible shanks 297 having sharps 279 on a distal end thereof and located within hollow bore 271 of flexible needle 270. Flexible needle 270 can have a sharp edge 272 at a distal end. Feeder mechanism 260 can comprise a movable pusher 262 that moves longitudinally within bore 271 for ejecting the stack of flexible shanks 297 therefrom. An adhesive injection system 290 can be provided with a longitudinally movable piston 291 located in a passageway 284 to force adhesive 100 from an orifice 284a of passageway 284.

In FIG. 6b, the flexible needle 270 containing the plurality of flexible shanks 297 has moved within passageway 287 to drive a distal end of flexible needle 270 and an end flexible shank 297 through tissue portions 105, 106.

In FIG. 6c, the flexible needle 270 has been withdrawn into passageway 287 to expose the flexible shank 297 captured in tissue portions 105, 106.

In FIG. 6d, the adhesive injection system 290 has been actuated by moving piston 291 longitudinally to inject adhesive 100 into second pocket 286, through an expanded hole in tissue portions 105, 106 formed by the flexible needle 270, and into the first pocket 285 to create adhesive fastener 295. Once the injection pressure is released, the tissue contracts and squeezes out the adhesive 100 about shank 297 and the tissue 105, 106 and fastener 295 can be released.

FIG. 6e my show a fully polymerized fastener 295 fastening two portions of tissue 105, 106 together, the fastener 245 comprising a first adhesive head 296, an adhesive shank 297, and the second adhesive head 298.

A Seventh Surgical Adhesive Fastener Device

FIG. 7a is a cross sectional view of a seventh surgical fastening device 325 having an end effector 330 clamped on two portions of tissue 105, 106 for the creation of a dual headed surgical fastener 345 having a first adhesive head 346, an adhesive shank 347, and a second adhesive head 348 formed on the opposite end of the adhesive shank 347. The surgical device 325 can have a plurality of flexible needles 320 movable within a plurality of curved passageways 345 for penetrating tissue and the simultaneous creation of a plurality of dual headed fasteners 345 from adhesive 100.

The end effector 330 is located at a distal end of a shaft 331 and can have a fixed jaw 332 and a movable clamping jaw 333. Clamping jaw 333 has a plurality of first pockets 335 within, and fixed jaw 332 has a plurality of opposing second pockets 336 within for forming first and second adhesive heads 346, 348 respectively. A plurality of curved passageways 345 are located in a fixed jaw 332 and each curved passageway 345 can contain the flexible needle 320 movable therein to direct each of the flexible needles 320 towards the second pocket 336 in movable clamping jaw 333. Each flexible needle 320 is operably connected to the next by a tube 340 and each needle 320 has a sharp edge 322 for piercing and cutting tissue and a bore 321. The bores 321 interconnect and contain an adhesive 100, and are operably coupled to an adhesive piston rod 342 longitudinally movable in a straight portion of bore 321. Distal movement of adhesive piston rod 342 forces adhesive 100 from an orifice 321a in each of the pluralities of flexible needles 320.

FIG. 7b shows the plurality of flexible needles 340 moved within the plurality of curved passageways 345 to penetrate the first and second portions of tissue 105, 106. Adhesive 100 is being ejected from each of the flexible needles 340 by moving adhesive piston rod 342 distally and adhesive 100 has filled each of the first pockets 335 within the movable jaw 332.

FIG. 7c shows the plurality of flexible needles 340 retracted through the first and second portions of tissue 105, 106 to place each adhesive shank 347 of adhesive fasteners 345 therethrough and attached to first head 346.

In FIG. 7d, the plurality of flexible needles 340 have retracted through the first and second portions of tissue 105, 106 and through the second pockets 336 back to the position of FIG. 7a. Adhesive continued to flow from each needle 340 during the retraction to fill each of the second pockets 336 with adhesive 100. In this view, the adhesive has just polymerized about tissue 105, 106 and is beginning to polymerize the adhesive in the first and second pockets 335, 336. The tissue can now be released.

FIG. 7e shows a fully polymerized fastener 345 fastening two portions of tissue 105, 106 together, the fastener 345 comprising first adhesive head 346 and the second adhesive head 348 formed on the shank 347.

An Eighth Surgical Adhesive Fastener Device

FIG. 8a is a cross sectional view of an eighth surgical fastening device 375 having an end effector 380 clamped on two portions of tissue 105, 106 for the creation of a dual headed surgical fastener 395 having a first adhesive head 396, an adhesive shank 397, and a second adhesive head 398 formed on the opposite end of the adhesive shank 397. The surgical device 375 can use a light curing polymerizable adhesive 100 in combination with a flexible needle 390 movable within a curved passageway 384 for penetrating tissue and the creation of dual headed fasteners 395 from adhesive 100.

The end effector 380 is located at a distal end of a shaft 381 and can have a fixed jaw 382 and a movable clamping jaw 383. Movable jaw 382 has a first pocket 385 within, and fixed jaw 382 has a second pocket 386 within for forming first and second adhesive heads 396, 398 respectively. The passageway 384 is located in fixed jaw 382 and contains the flexible needle 370 movable therein. Flexible needle 370 has a sharp edge 372 for piercing tissue and a bore 371 containing polymeric adhesive 100 that can be injected therefrom and rapidly polymerized by UV light into the adhesive fastener 95. An adhesive injection system 390 may have a piston rod 391 longitudinally movable in bore 371 to force adhesive 100 from bore 371 into second pocket 383, through the tissue 105, 106 and into the first pocket 385.

An optical fiber 376 extends from shaft 381 into movable clamping jaw 383 for the passage of ultraviolet light. A mirror 377 is located at a distal end of the optical fiber 376 to divert the UV light into the adhesive 100 in the jaws 382, 383 and tissue 105, 106. The application of light, such as UV light polymerizes the adhesive 100 to form fastener 395.

A Ninth Surgical Adhesive Fastener Device-Distal Pin Fastener

Figure 9A:
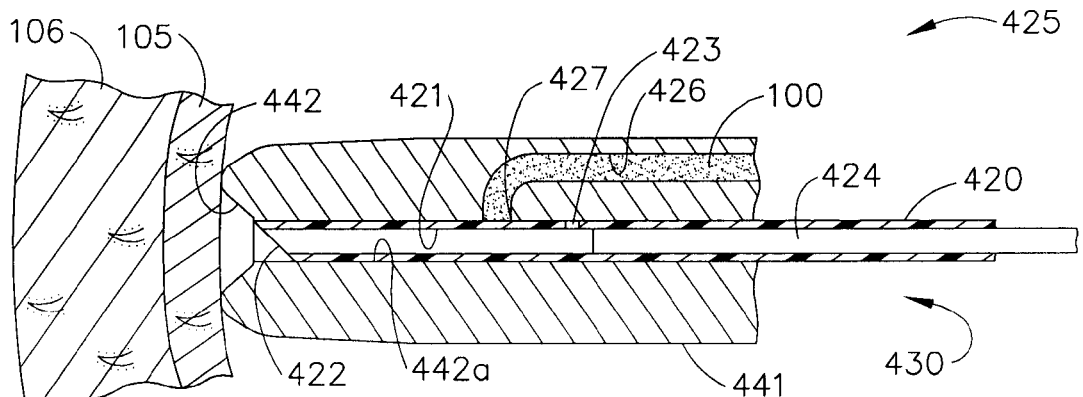
FIG. 9a is a cross sectional view of a ninth adhesive fastening device for placing an adhesive fastener from a distal end of the surgical fastening device to secure two portions of tissue together and having a piercing system and an adhesive injection system.

FIG. 9a is a cross sectional view of a ninth surgical fastening device 425 having an end effector 430 capable of placing a distally extending adhesive surgical pin fastener 445 from a distal end of the surgical device 425 to hold two portions of tissue 105, 106 together. The pin fastener 445 is created from an adhesive 100 and can have a first adhesive head 446 at a proximal end and an adhesive pin 447 extending distally therefrom and into tissue.

Surgical fastening device 425 has an elongated shaft 441 with a conical opening 442 in the distal end, and a passageway 442a extending therefrom longitudinally into shaft 441. A piercing needle 420 can reciprocate within passageway 442a and can have a hollow 421 therein, a point 422 at a distal end, and an opening 423 located in the side of the piercing needle 420. A plunger 424 is slidably located within the piercing needle 420. An adhesive passage 426 is provided in shaft 441 and has an orifice 427 engaging with passageway 442a. A pressurized adhesive 100 is located within adhesive passage 426 and contained therein by piercing needle 420 blocking orifice 427.

In FIG. 9a, the piercing needle 420 is withdrawn into passageway 442a and adhesive flow is prevented by piercing needle 420 blocking orifice 427. A distal end of plunger 424 is located proximal to opening 423.

Figure 9B:
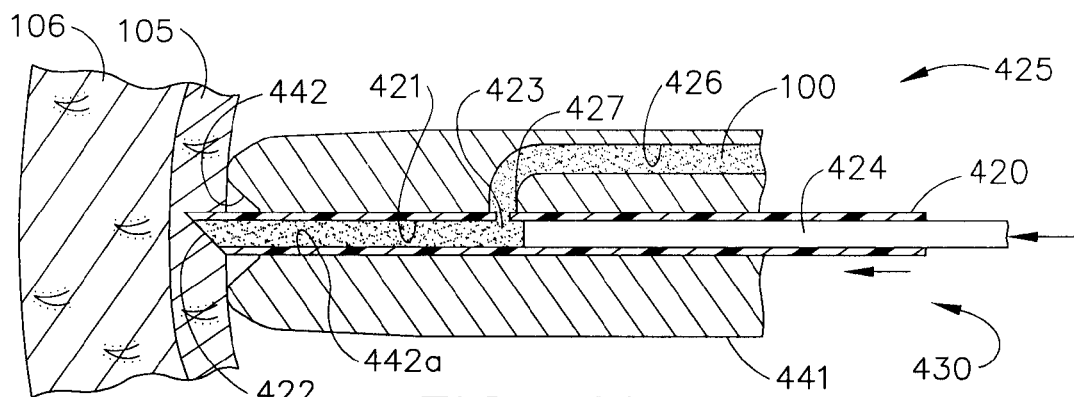
FIG. 9b is a cross sectional view of the ninth adhesive fastening device as a piercing needle of the piercing system penetrates tissue and adhesive is injected into the piercing needle.

In FIG. 9b, the piercing needle 420 and plunger 424 are moved distally to pierce the first portion of tissue 105 and to place opening 423 within the piercing needle 420 into alignment with orifice 427 of the adhesive bore 426. Pressurized adhesive 100 has flowed from adhesive bore 426, through orifice 427, through opening 423 and has filled the hollow 421 within piercing needle 420 from point 422 to plunger 424.

Figure 9C:
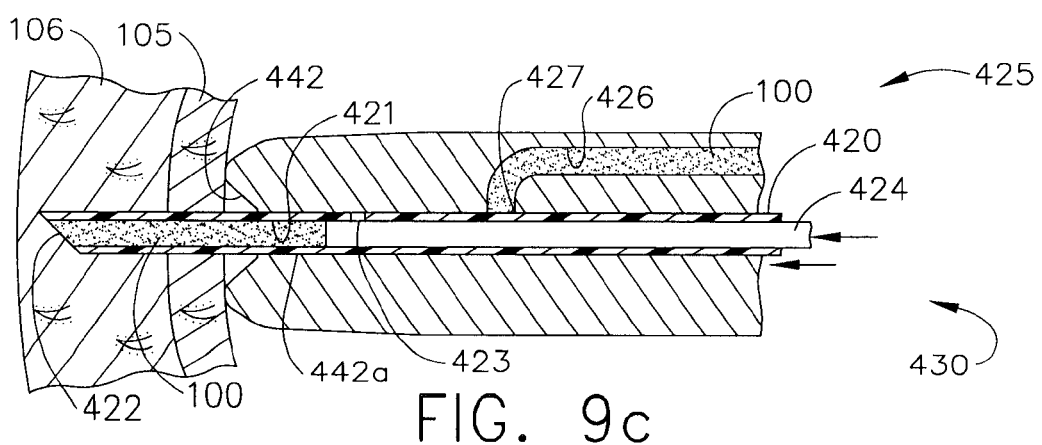
FIG. 9c is a cross sectional view of the ninth adhesive fastening device with the piercing needle of the piercing system penetrated into tissue.

In FIG. 9c the piercing needle 420 and plunger 424 are moved distally a second amount to pierce into both the first and second portions of tissue 105, 106 and to move opening 423 in the piercing needle 420 past orifice 427 of the adhesive bore 426 to block the flow of additional adhesive 100 therefrom.

Figure 9D:
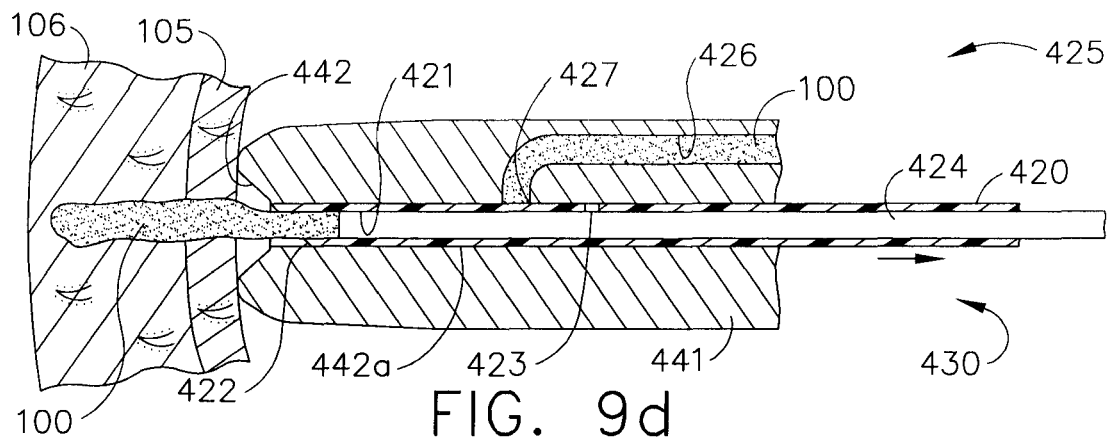
FIG. 9d is a cross sectional view of the ninth adhesive fastening device with the piercing needle of the piercing system retracted into the adhesive fastening device to leave an adhesive fastener in tissue.
Figure 9E:
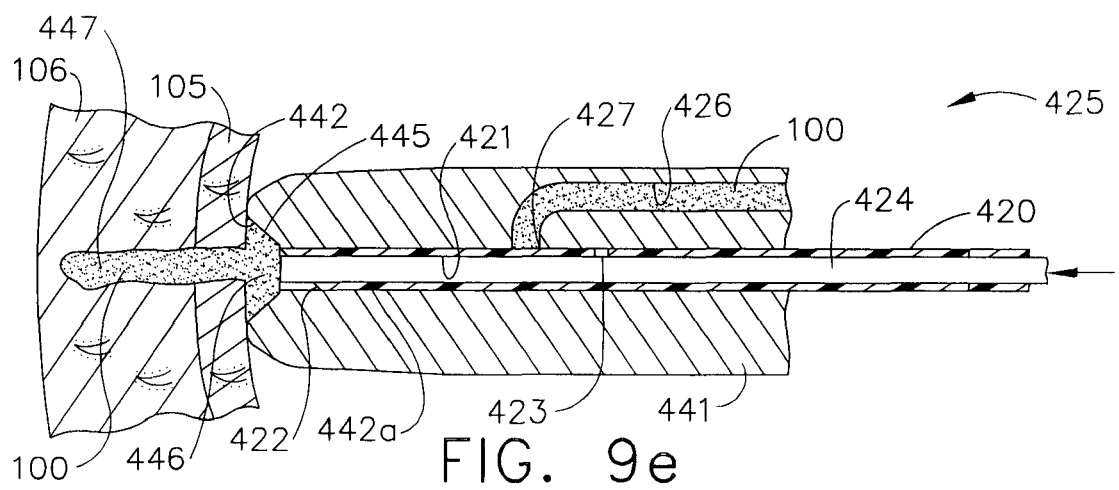
FIG. 9e is a cross sectional view of the ninth adhesive fastening device of FIG. 9d with a head formed on the adhesive fastener in tissue.
Figure 9F:
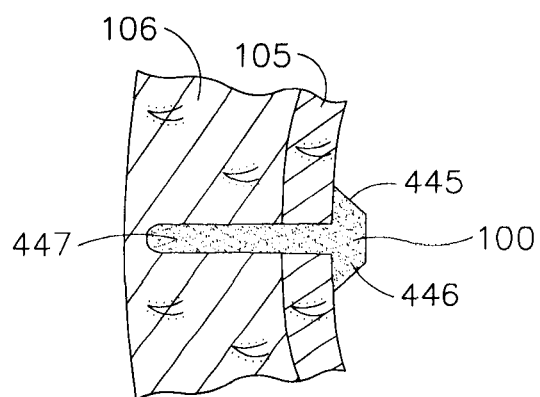
FIG. 9f is a cross sectional view of the adhesive fastener with a head securing two portions of tissue together in tissue.

In FIG. 9d the piercing needle 420 may retract proximally back to the position of FIG. 9a while plunger 424 can remain fixed. This can disperse adhesive 100 from the retracting piercing needle 420 to create pin 447 within tissue 105, 106. In FIG. 9e, the plunger 424 has moved distally to force the remainder of the adhesive 100 into conical opening 442 to create the adhesive head 446 at the end of adhesive shank 447.

FIG. 9e shows the surgical fastening device 425 removed from the surgical site and the pin fastener 445 formed from polymerized adhesive 100 holding tissue portion 105 onto tissue portion 106.

A Tenth Surgical Adhesive Fastener Device-Multiple Pin Fasteners

Figure 10A:
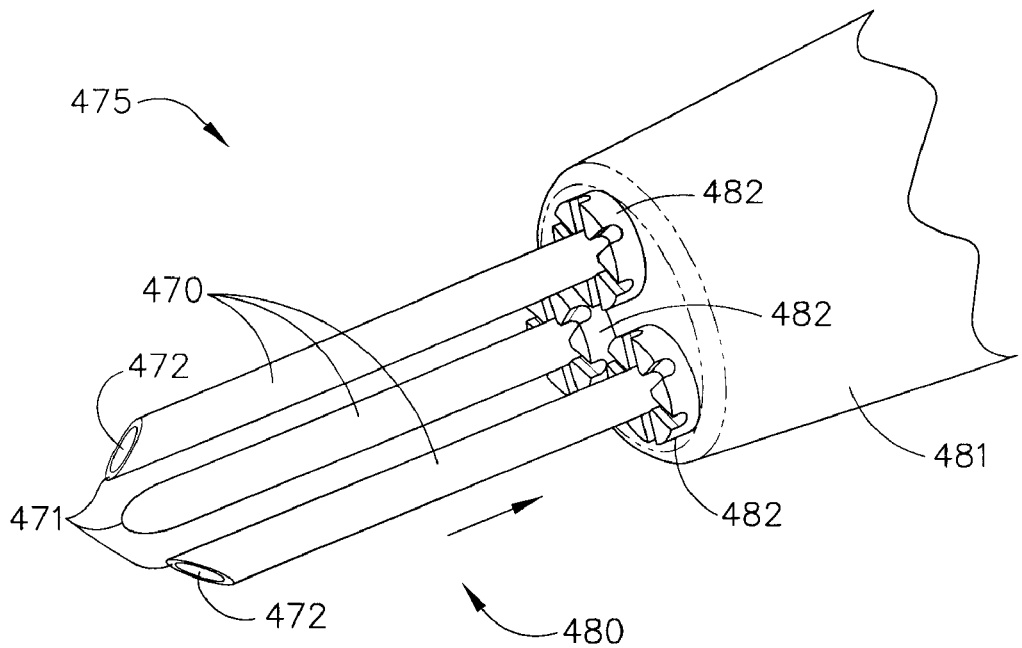
FIG. 10a is an isometric view of a tenth adhesive fastening device for forming a plurality of adhesive fasteners from a distal end of the surgical device.

FIG. 10a is an isometric view of a tenth surgical fastening device 475 having an end effector 480 capable of placing a plurality of adhesive surgical pin fasteners 495 from a distal end of the surgical device 475 to hold two portions of tissue 105, 106 together. The surgical fastening device 475 is an alternate embodiment of the ninth surgical fastening device 425 and can combine at least two of the identical mechanisms described previously placed side by side in a shaft 481 to create multiple fasteners simultaneously. Thus surgical fastening device 475 can place multiple pin fasteners 495 created from an adhesive 100. Each fastener 495 can have a star shaped first adhesive head 496 at a proximal end, and an adhesive pin 497 extending distally therefrom and into tissue.

In FIG. 10a, a plurality of hollow injection needles 470 are extended distally from a shaft 481 of the surgical device 475. Each injection needle 470 has a sharp edge 471 at a distal end, a hollow 472 extending longitudinally therethrough and is operably connected to an adhesive pump or pressurized chamber for dispensing the polymerizable adhesive 100. A plurality of head forms 482 are fixedly located at a distal end of shaft 481 to form adhesive heads 496.

Figure 10B:
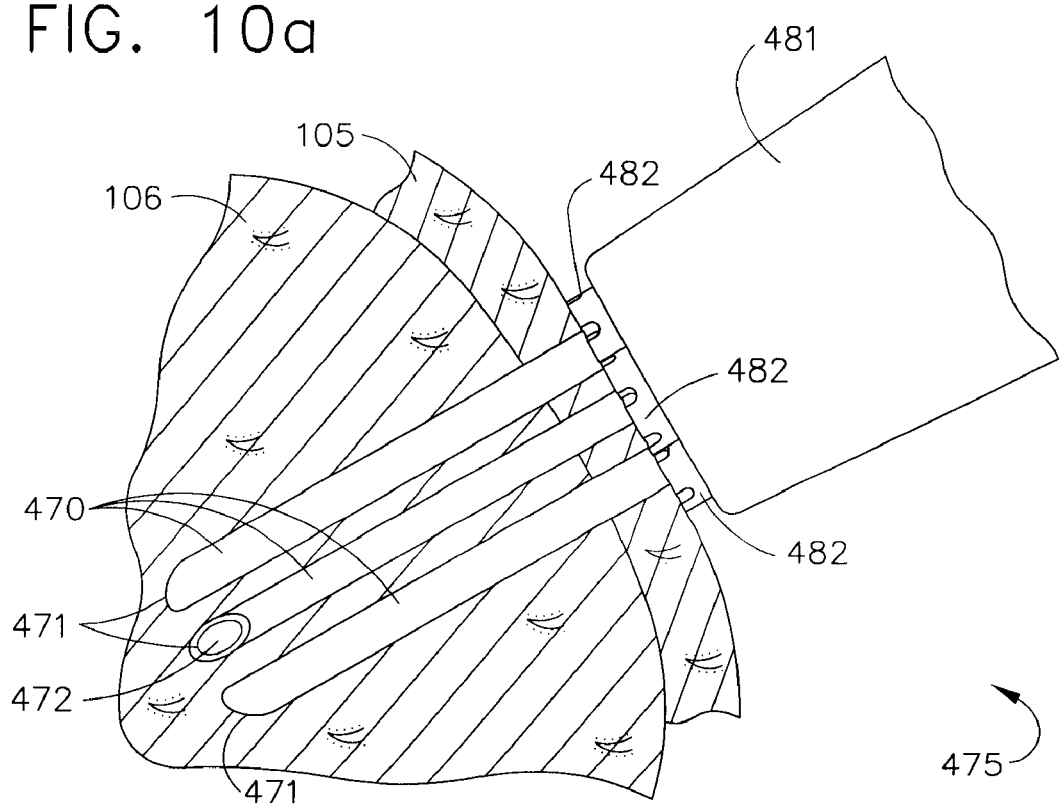
FIG. 10b is a cross sectional view of the tenth adhesive fastening device inserted into two portions of tissue.
Figure 10C:
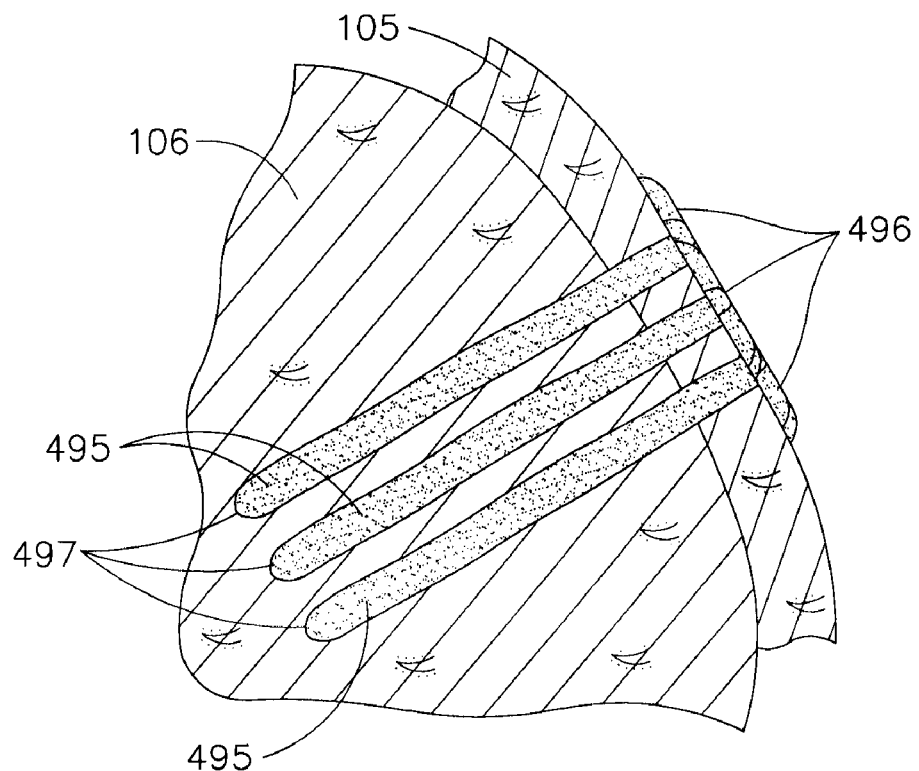
FIG. 10c is a cross sectional view of the headed adhesive fasteners formed by the tenth surgical fastening device to secure the two portions of tissue together.
Figure 10D:
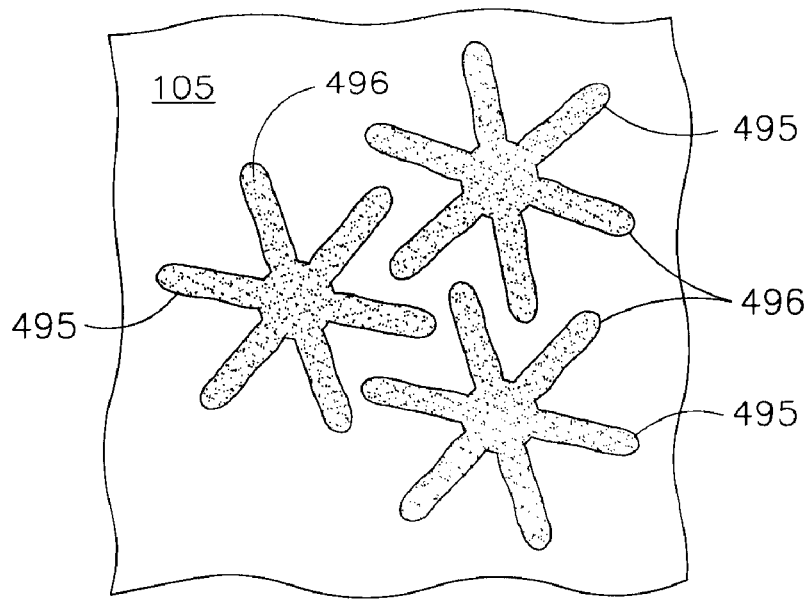
FIG. 10d is a top view of the headed adhesive fasteners formed by the tenth adhesive fastening device.

FIG. 10b shows the plurality of hollow injection needles 470 placed into first and second portions of tissue 105, 106. FIGS. 10c and 10d show side and end views of pin fasteners 495 created from an adhesive 100. Each fastener 495 can have a star shaped first adhesive head 496 at a proximal end, and an adhesive pin 497 extending distally therefrom and into tissue.

An Eleventh Surgical Clamp Adhesive Fastener Device with Injector

Figure 11A:
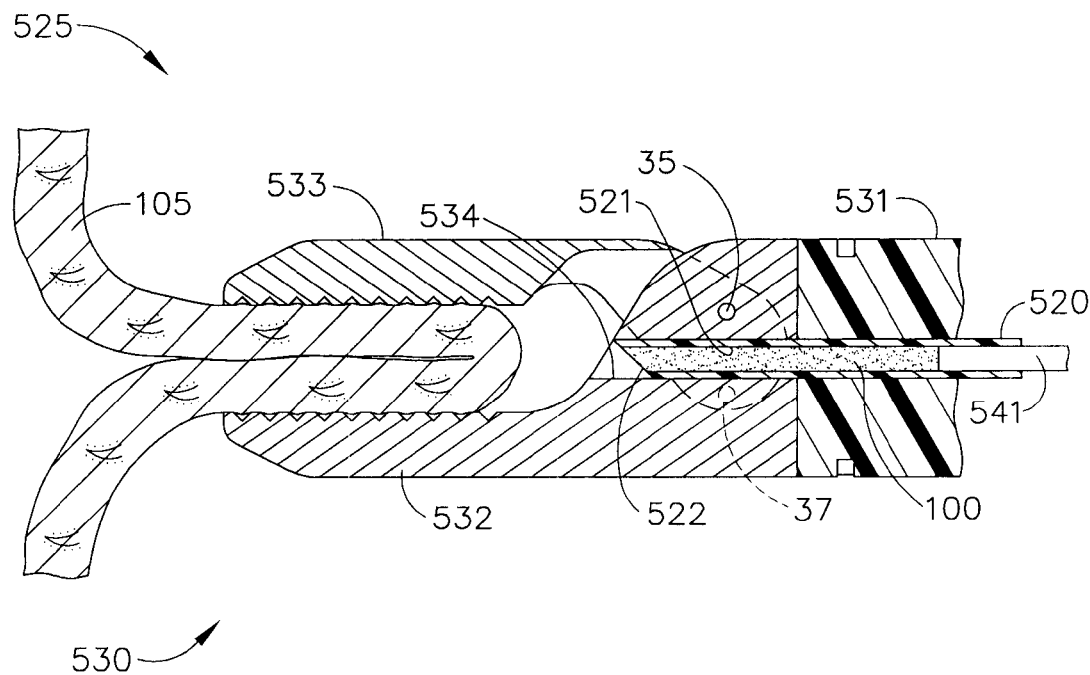
FIG. 11a is a cross sectional view of an eleventh adhesive fastening device clamping tissue and having a piercing system and an adhesive injection system having an adhesive fastener system, the eleventh surgical fastening device for placing an adhesive fastener from a distal end of the surgical fastening device to secure tissue together.
Figure 11B:
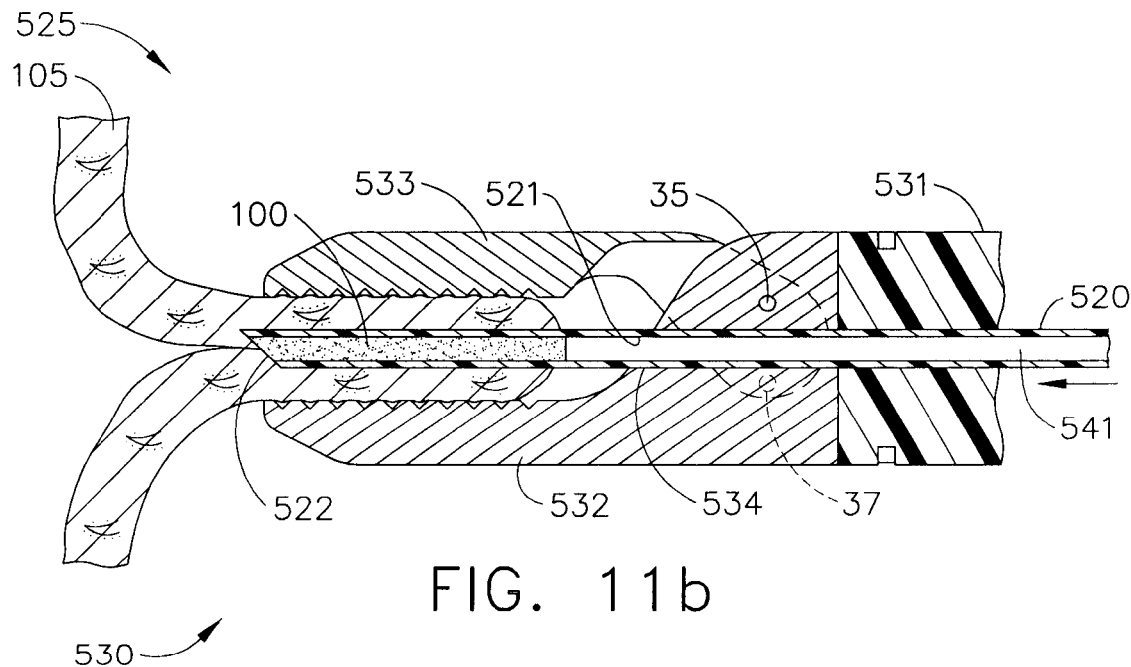
FIG. 11b is a cross sectional view of the eleventh adhesive fastening device as a piercing needle of the piercing system penetrates tissue and adhesive is injected into the piercing needle.

FIGS. 11a and 11b can show cross sectional views of an eleventh alternate embodiment of an adhesive fastening device 525 for creating form in place fasteners from an adhesive 100. The surgical device 525 can clamp onto folded tissue 105 and can inject an adhesive fastener 545 into the clamped adhesive to fasten the adhesive together. As shown in FIG. 11 the surgical fastening device 525 can have an end effector 530 clamped on a folded portion of tissue 105. End effector 530 can be located at a distal end of a shaft 531 and can have a movable clamping jaw 533 and a fixed jaw 532. A passageway 534 is located in fixed jaw 532 and contains a longitudinally movable needle 520 therein. Needle 520 has a sharp edge 522 for piercing and cutting tissue and a bore 521 containing a polymeric adhesive 100 therein. A piston rod 541 is longitudinally movable in bore 521 to force adhesive 100 from needle 520.

Figure 11C:
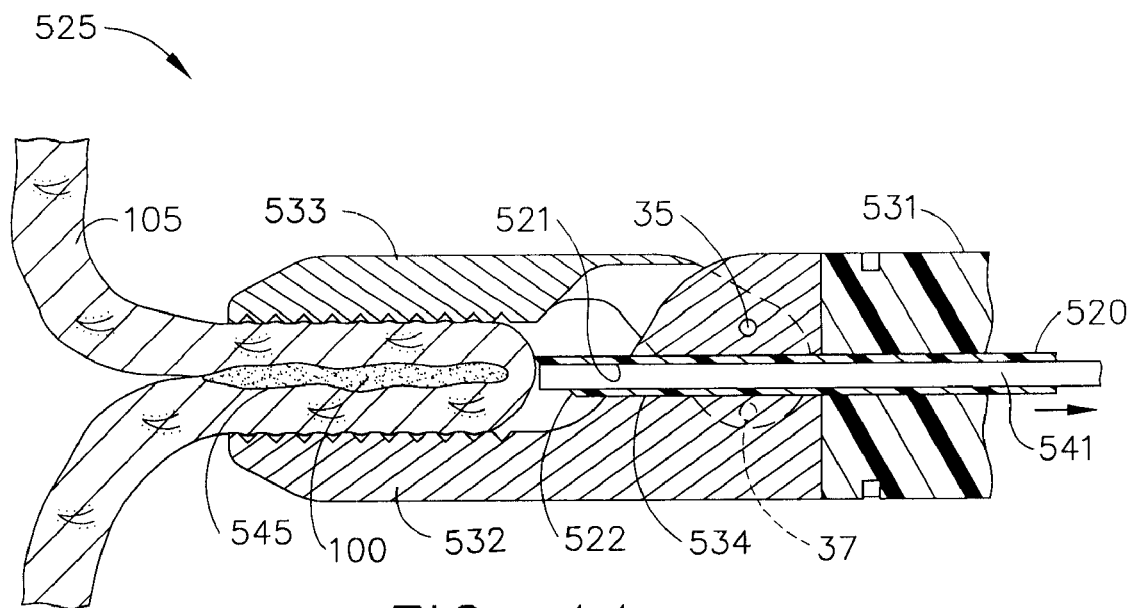
FIG. 11c is a cross sectional view of eleventh adhesive fastening device with a piercing needle of the piercing system withdrawn from tissue and leaving adhesive to secure tissue together therein.
Figure 11D:
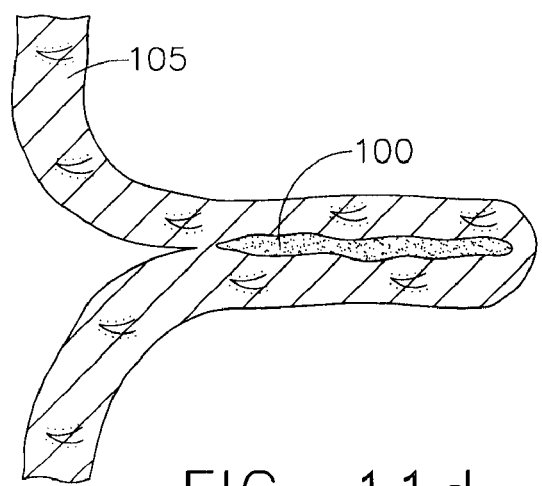
FIG. 11d is a cross sectional view of the tissue adhered together with the eleventh adhesive fastening device.

In FIG. 11b, the needle 520 and the piston rod 541 have moved distally as a unit to pierce folded tissue 105. In FIG. 11c, the needle 520 has been withdrawn from the tissue 105 to dispense adhesive 100. After withdrawal of the needle 520, the piston rod 541 is withdrawn to the position shown and the adhesive is polymerizing from tissue contact. FIG. 11d shows the healed tissue that has grown around polymerized adhesive 100.

Detachable Adhesive Head for a Form in Place Fastener Device

Figure 12A:
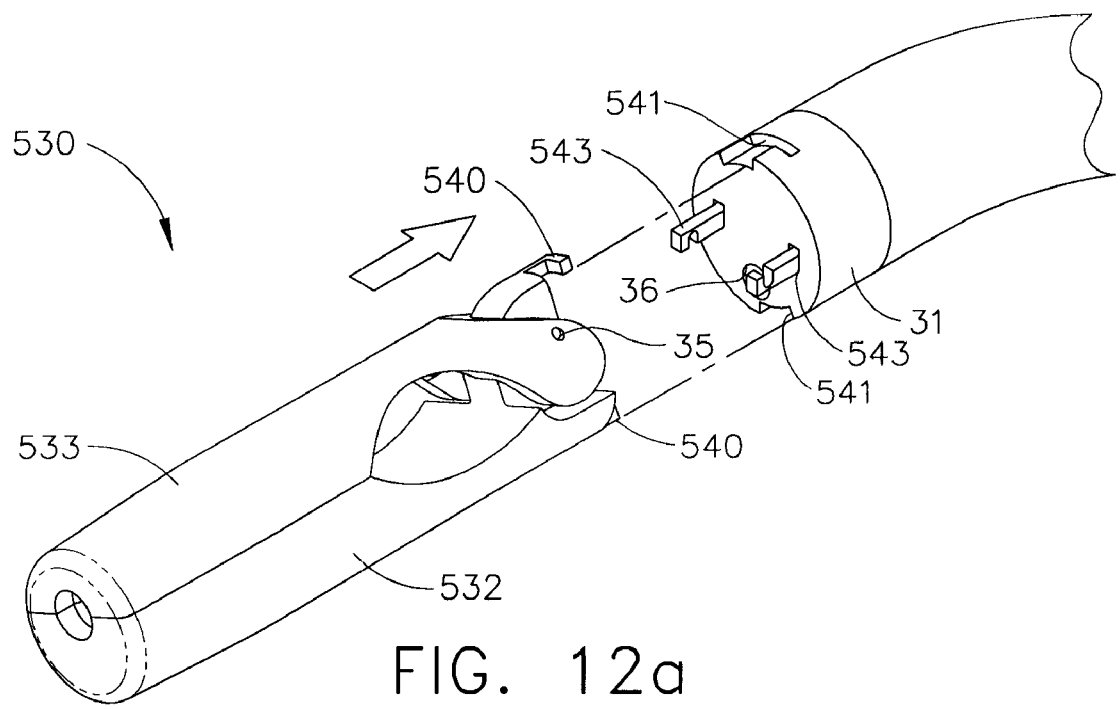
FIG. 12a is an isometric view of a detachable application head of a twelfth adhesive fastening device.
Figure 12B:
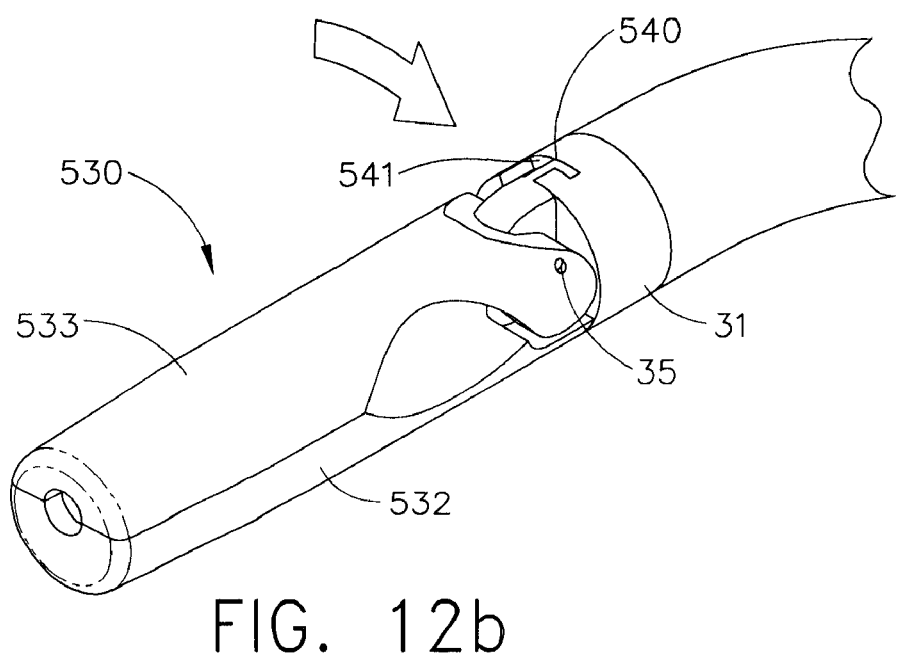

FIGS. 12a and 12b can show a mechanism for attaching any of the embodiments of end effectors listed above and below to a surgical shaft 31. Surgical shaft 31 may be shown and described in the first example above and can have a reciprocating actuator rod 36 that may operatively engage with a movable or pivotable clamp jaw such as clamp jaw 533. A pair of hooks 540 can extend from a fixed lower jaw 532 of end effector 530 to releasably lock in a mating pair of receptacles 541 in surgical shaft 31 by a twisting action in the direction of the arrow. A pair of shaft hooks 543 can extend from the shaft 31 and engage with pin 35 that the clamp jaw such as clamp jaw 582 pivots about. This twisting action also engages reciprocating actuator rod 36 with a pivotable clamp jaw such as clamp jaw 582. Reversal of the twisting action enables the end effector, such as end effector 533 to be removed. This detachable head design can be well suited to adhesive fastener forming end effectors as clogged or glued together end effectors can easily be discarded and replaced with a clean new end effector.

A Twelfth Embodiment of an Adhesive Fastener Device

FIGS. 13a-13e show the steps of use of a twelfth embodiment of an alternate embodiment of a surgical form in place fastening device 575 for creating an adhesive fastener 595 about an anatomical vessel. FIGS. 14a to 14c are a series of cross section of the fastening device 575 and vessel as the adhesive fastener 595 is created.

Figure 13A:
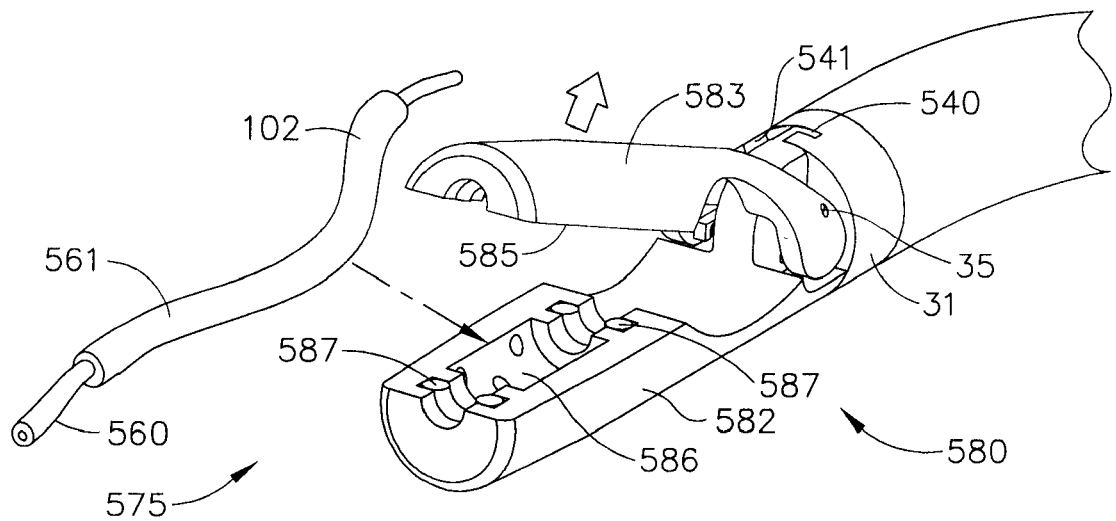
FIG. 13a is an isometric view of the opened application head of the twelfth adhesive fastening device as a vessel surrounded by a bandage is placed within a pair of movable clamp jaws of the application head.
Figure 13B:
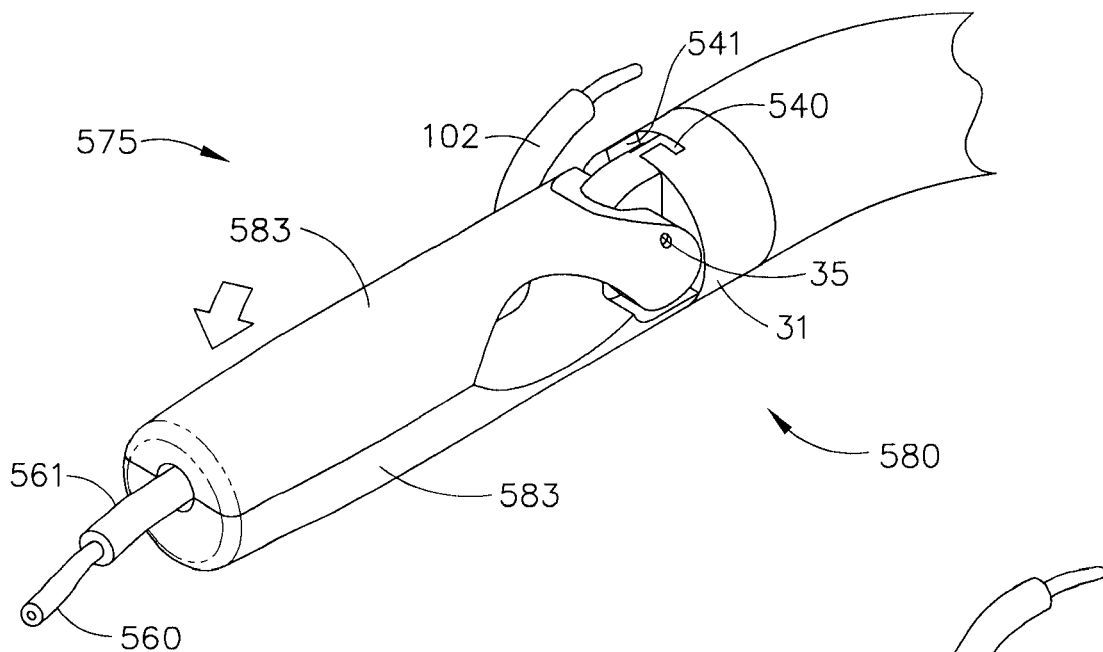
FIG. 13b is an isometric view of the application head of the twelfth adhesive fastening device clamped around the vessel surrounded by a bandage and injecting adhesive into the bandage.
Figure 13C:
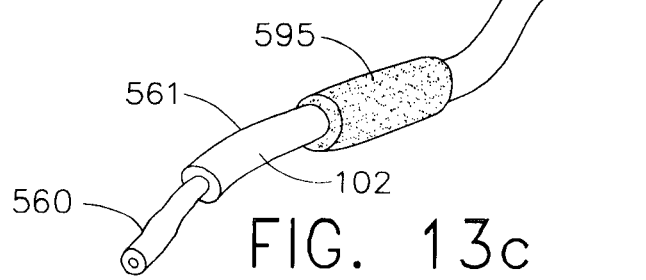
FIG. 13c is an isometric view of the adhesive saturated bandage sealing and reinforcing the vessel.
Figure 14A:
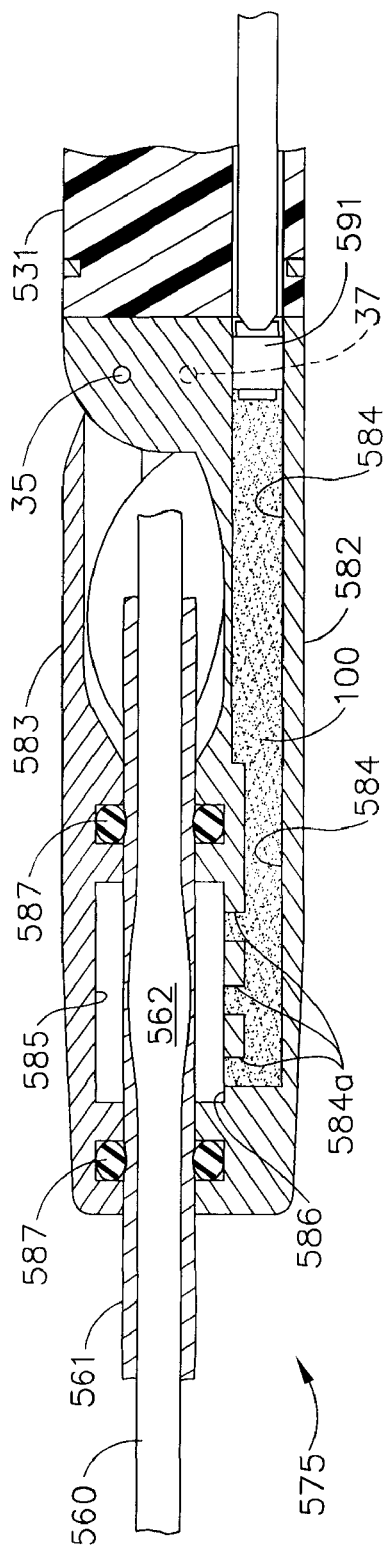
FIG. 14a is a cross sectional view of the detachable application head of the twelfth adhesive fastening device clamped on tissue showing the thinned walls of the vessel clamped between jaws and an adhesive injection system.
Figure 14B:
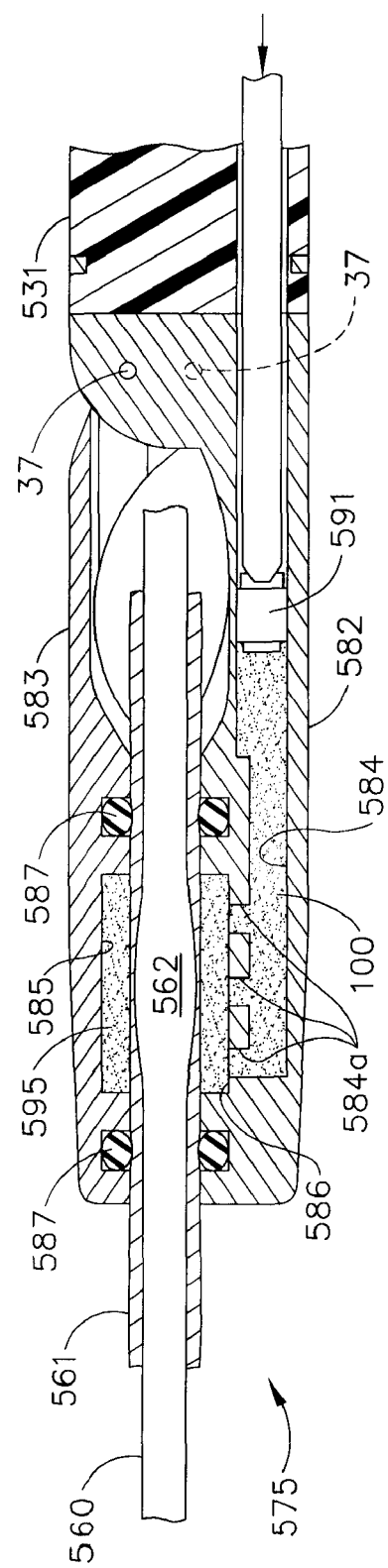
FIG. 14b is a cross sectional view of the detachable application head of the twelfth surgical fastening device clamped on tissue showing the injection of adhesive to saturate the bandage.
Figure 14C:
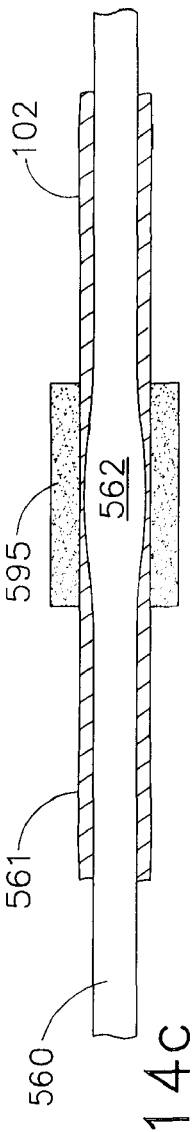
FIG. 14c is a cross sectional view of the adhesive saturated bandage sealing and reinforcing the vessel.

In FIG. 13a, an end effector 580 of the fastening device 575 is shown next to a vessel 560 that is surrounded by a bandage 560. A pivotable jaw 583 is shown opened relative to a fixed jaw 582. Both the pivotable jaw 583 and fixed jaw 582 contain a pivotable receptacle 585 and a fixed receptacle 586 for the reception of the vessel 560 and bandage 561 therein. Seals 587 are located at either end of receptacle 586, 585 for sealing with the vessel 560 and bandage 561. In FIG. 13b, the vessel 560 and bandage 561 are clamped within the jaws 582 and 583 and the polymerizable adhesive 100 is flooding the receptacles 586 and 585. For this example, an adhesive initiator 102 can be drawn or wicked within bandage 561 to polymerize the adhesive. When the movable jaw 582 opens, the vessel 560, bandage 561 and fastener 595 of formed polymerized adhesive 100 is released as shown in FIG. 13c. Bandage 560 could be constructed from bioabsorbable or biodegradable materials such as but not limited to polylactic acid, polyglycolic acid, polyglactin, polydioxanone, polyglyconate. silk, nylon, polypropylene, braided polyester, polybutester, polyethylene, and polyetheretherketones (PEEK).

Turning now to FIGS. 14a-14c, cross sectional views of the fastening device 575 are shown as the adhesive fastener 595 is formed about vessel 560 and bandage 561. In FIG. 14a, the pivotable jaw 583 and fixed jaw 582 are shown clamped about vessel 560 and bandage 561. Vessel 560 has an aneurism 562 or expansion and thinning of the vessel walls. To reinforce the vessel 560 and prevent rupture, bandage 561 is placed about the aneurism 562. Closure of the jaws has caused vessel 560 to engage soft elastomeric flexible pads or seals 587 to seal each end of the vessel 560. A passageway 584 contains an adhesive 100 and has one or more orifices 584a that operatively connect with the receptacles 586. A longitudinally movable piston 591 is provided to dispense adhesive from passageway 584.

In FIG. 14b, the movable piston 591 has moved distally to push adhesive 100 through orifices 584a and into the chamber formed from receptacles 586 and 585. Adhesive flow about vessel 560 is prevented by seals 587 as the chamber is filled as shown. The adhesive is polymerized by the adhesive initiator 102 in the bandage 561.

FIG. 14c shows how aneurism 562 is surrounded with bandage 561 and adhesive fastener 595. Alternately, bandage 561 can be porous enabling adhesive 100 to penetrate the bandage 561 and adhere directly to vessel tissue.

A Thirteenth Embodiment of an Adhesive Fastener Device

Figure 14D:
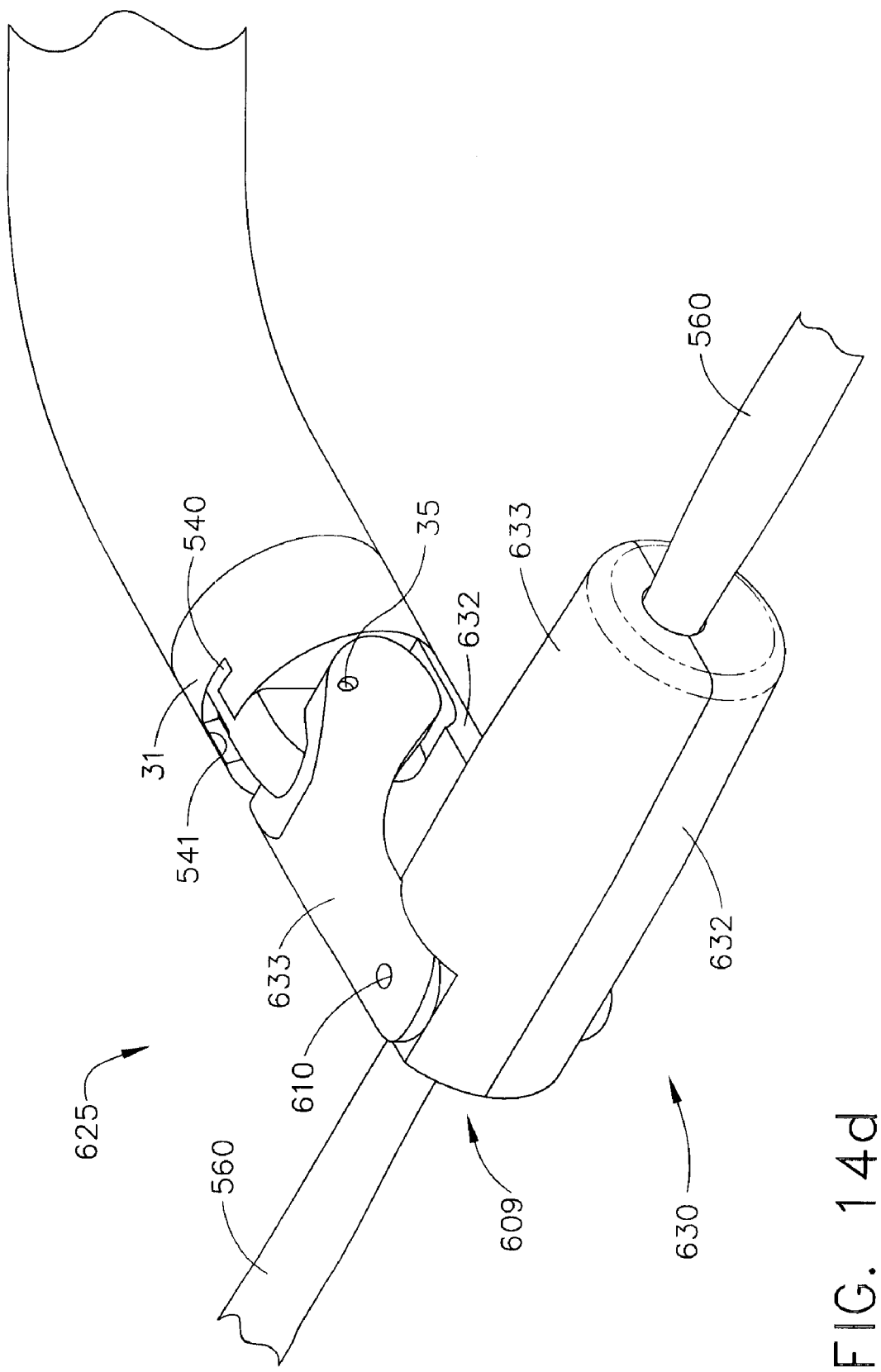
FIG. 14d is an isometric view of a first alternate embodiment of the twelfth adhesive fastening device having a laterally pivotal head to capture vessels at an angle to the surgical device.

FIG. 14d can show an additional embodiment of the surgical fastening device shown in FIGS. 13a-13b including an additional pivot joint 609 to enable pivoting of the end effector as shown. The surgical fastening device 625 has an end effector 630 with a split jaws 632 and 633 that can pivot about a pin 610. A detent 634 (not shown) can be provided to detent the end effector 630 at a series of angles.

A Fourteenth Embodiment of an Adhesive Fastener Device

Figure 15C:
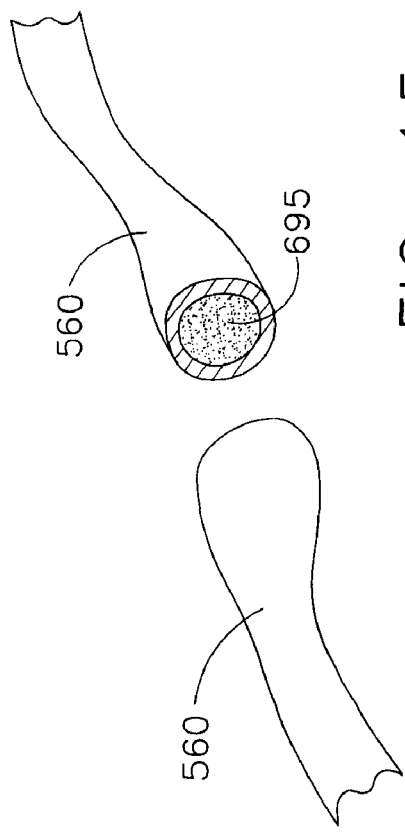
FIG. 15c is an isometric view of the severed vessel of FIG. 15b showing the adhesive plug formed therein.
Figure 15D:
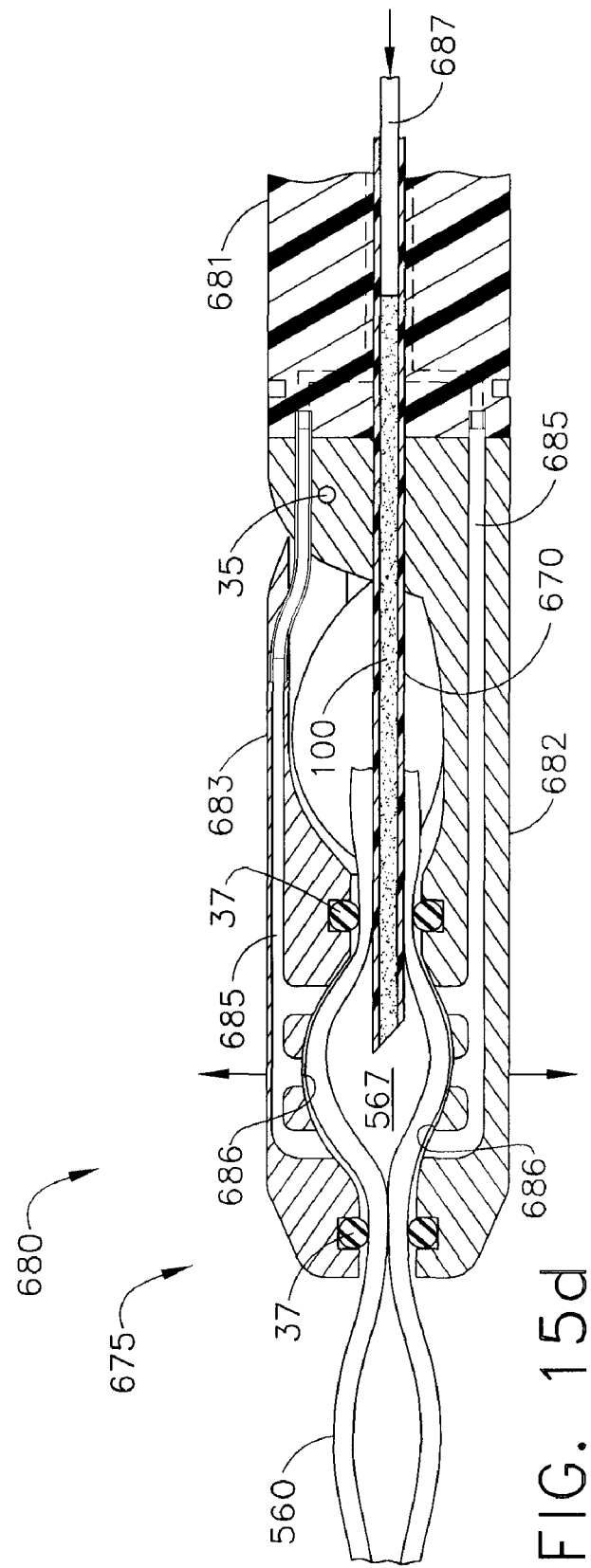
FIG. 15d is a cross sectional view of the second alternate embodiment of the twelfth surgical fastening device using a vacuum system to expand the vessel and an adhesive injection piercing the vessel prior to injecting the adhesive plug therein.

FIGS. 15a-15d show a fourteenth embodiment of a surgical fastening device 675 having an end effector 680 for that uses vacuum to create an adhesive fastener 695 within an anatomical vessel 560. The end effector 680 is attached to shaft 681 and has a pivotable jaw 683 and a fixed jaw 682 and vacuum ports 685. Pivotable jaw 683 is shown closed on vessel 560 and a vacuum is being applied from vacuum ports 685 to expand the vessel 560 within a vacuum chamber 686. A longitudinally movable hollow adhesive needle 670 can be filled with adhesive 100 and can extend through fixed jaw 683 aimed at the vessel 560. As shown in FIG. 15d, distal movement of adhesive needle 670 pierces vessel 560 and enables polymerizable adhesive 100 to be pumped into a lumen 567 of vessel 560 with piston 687. The vessel 560 fills with adhesive 100 which polymerizes to create the fastener 695 within vessel 560 as shown in FIG. 15b. FIG. 15c is a cross section of the severed vessel 560 with adhesive fastener 695 fastened therein.

A Fifteenth Embodiment of a Circular Adhesive Fastener Device

Figure 16A:
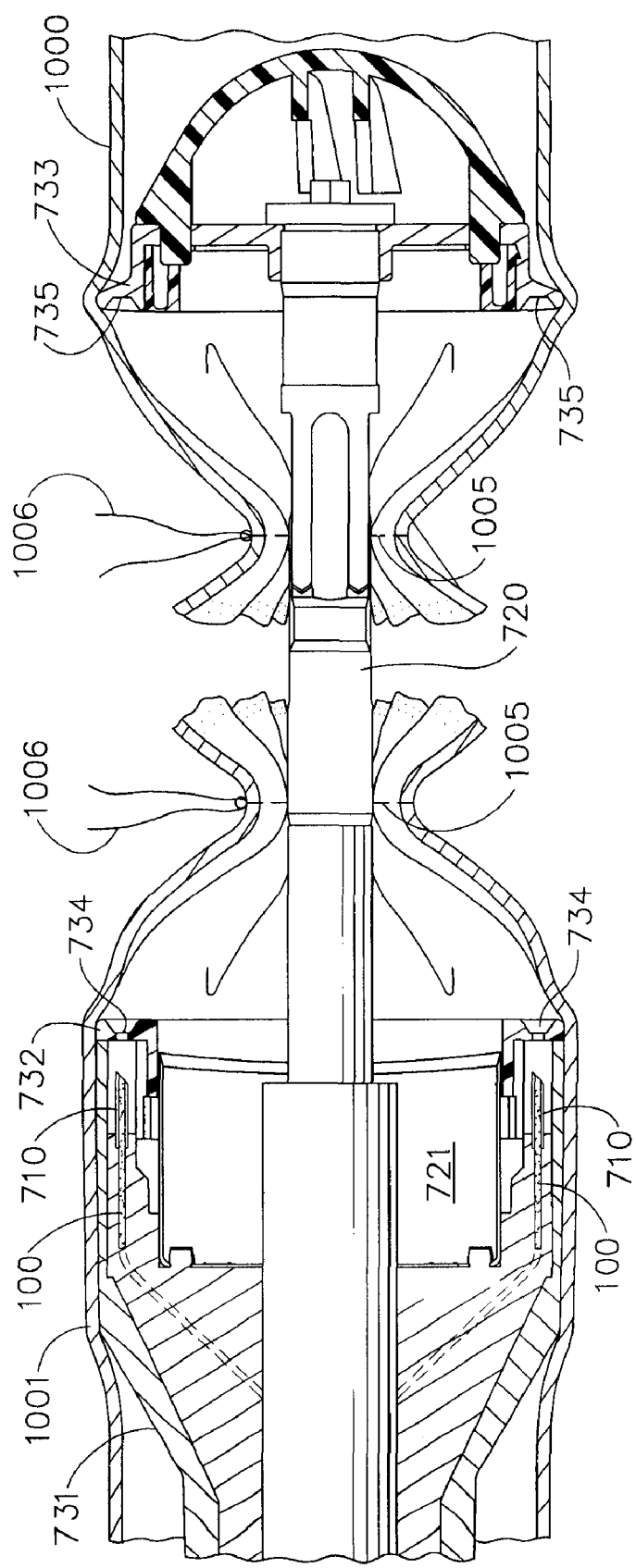
FIG. 16a is a cross sectional view of a circular stapler for clamping a pair of portions of luminal tissue together and an adhesive injection system to place one or more circular arrays of adhesive fasteners to join the first and second portions of luminal tissue together.

FIGS. 16a-16d show a cross section of a fifteenth embodiment of a surgical fastening device 725 for joining two luminal vessels such as intestines with a plurality of dual headed adhesive fasteners. The surgical device 725 is a new embodiment of a well known circular stapler that has the one or more circular row staples replaced with a plurality of adhesive fasteners 745. As shown in FIG. 16a the circular adhesive fastener device 725 has a fixed proximal jaw 732 and a movable jaw 733 to clamp tissue therebetween. Movable jaw 733 is shown in the open position and surrounded by a first portion of luminal tissue 1000 that is cinched in about a shaft 720 of the movable jaw 732 with a purse string 1005 of suture 1006. The fixed jaw 732 is also placed within a second portion of luminal tissue 1001 and cinched therein about shaft 720 with a purse string 1005 of suture 1006. A movable circular knife 721 is located within head 731 and is surrounded by and operably coupled with one or more rings of adhesive needles 710. The adhesive needles 710 contain polymerizable adhesive 100 and are operably coupled to an adhesive pump (not shown) to pump adhesive from adhesive needles 710. Fixed jaw 732 has a plurality of fixed pockets 734 aligned for reception of adhesive needles 710 and movable jaw movable jaw 733 has a plurality of movable pockets 735 also aligned for reception of adhesive needles 710 therein.

In FIG. 16b, the movable jaw 733 is closed adjacent to the fixed jaw 732 to clamp luminal tissue 1000, 1001 therebetween.

Figure 16C:
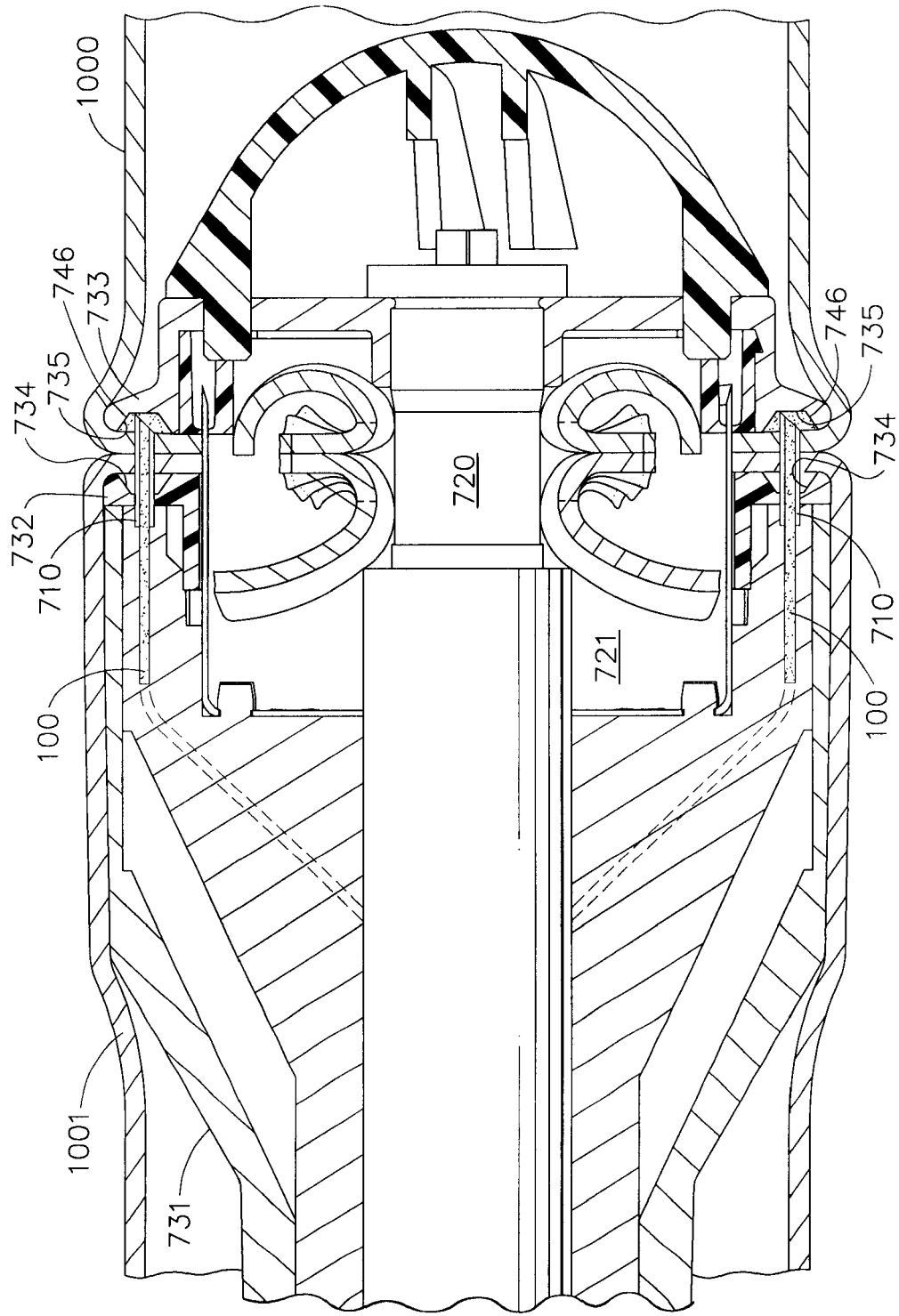
FIG. 16c is a cross sectional view of the circular stapler of FIG. 16b being fired to pierce the portions of luminal tissue with a plurality of piercing needles of the adhesive injection system and prior to injection of adhesive to secure the two portions of tissue together.
Figure 16D:
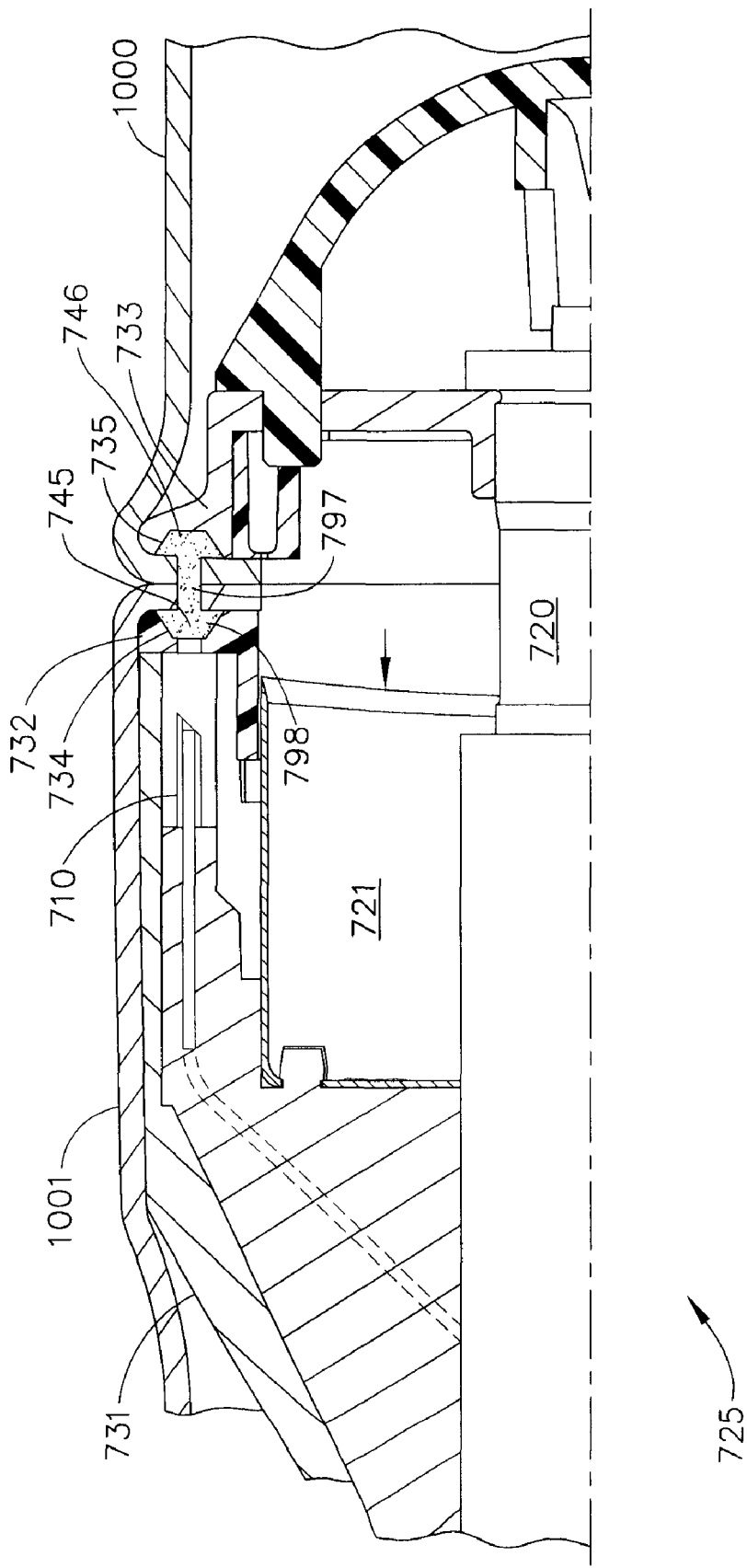
FIG. 16d is a partial cross sectional view of the circular stapler of FIG. 16b after being fired with the plurality of piercing needles withdrawn and a plurality of dual headed adhesive fasteners formed to secure the two portions of luminal tissue together.

In FIG. 16c, the surgical device 725 is fired to both sever the luminal tissue 1000, 1001 with circular knife 721 and to advance the rows of adhesive needles 710 through fixed pockets 734 and into movable pockets 735.

In FIG. 16c, the adhesive pump has forced adhesive 100 from the adhesive needles 710 to fill movable pockets 735 to create a first head 746 of the adhesive fastener 745. As the adhesive needles are withdrawn through tissue 100, 1001 with the adhesive pump engaged, adhesive flows into the holes punched by needles 710 to form adhesive shanks 797. As the needles 710 continue to retract through the fixed pockets 734 adhesive 100 fills the pockets 734 to create a second head 798 attached to the shank 797. Once the adhesive polymerizes from contact with the tissue, the movable jaw 733 can be opened to release the tissue 1000, 1001 joined together with one or more rings of dual headed fasteners 795. Surgical device 725 can now be removed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, whereas a plurality of examples of adhesive materials are disclosed that can be used to create adhesive fasteners, the invention of the present disclosure is not limited to those adhesives.

What is claimed is:

1. A surgical device for forming adhesive fasteners in one or more portions of tissue comprising:
    a) a shaft;
    b) a first jaw extending from a distal end of the shaft and a second jaw at the distal end of the shaft, the second jaw movable from a first position spaced away from the first jaw to a second position adjacent to the first jaw to clamp tissue therebetween, wherein the first jaw has a first head forming pocket, wherein the second jaw has a second head forming pocket;
    c) a fluid polymer adhesive contained within the surgical device, the fluid polymer adhesive polymerizable by exposure to an adhesive initiator; and
    d) a fastener forming end effector configured to form an adhesive pin fastener in tissue with the fluid polymer adhesive, wherein the fastener forming end effector is operable to form the adhesive pin by dispensing part of the fluid polymer adhesive in the first head forming pocket and part of the fluid polymer adhesive in the second head forming pocket, such that the adhesive pin fastener has two heads adjacent to opposite surfaces of the clamped tissue, wherein at least a part of the adhesive pin fastener is formed by shaping the fluid polymer adhesive while the end effector is in contact with the one or more portions of tissue, and polymerizing the fluid polymer adhesive by exposing the shaped fluid polymer adhesive to the adhesive initiator.

2. The surgical device of claim 1 wherein the fastener forming end effector is connected to a pump comprising a piston in a bore for dispensing the fluid polymer adhesive from within the surgical device and into contact with the one or more portions of tissue.

3. The surgical device of claim 2 wherein the adhesive initiator is one selected from the group consisting of tissue contact, visible light, ultraviolet radiation, heat, moisture, and polymerization initiating compounds.

4. The surgical device of claim 3 wherein the adhesive initiator is a polymerization initiating compound on at least a portion of the first jaw and the second jaw.

5. The surgical device of claim 1 further including a hollow needle filled with the adhesive reciprocatably mounted within the shaft and operably coupled to the fastener forming end effector to penetrate the one or more portions of tissue clamped between the first jaw and the second jaw, wherein when the hollow needle penetrates the one or more portions of tissue, wherein the fastener forming end effector is operable to place the fluid polymer adhesive within the one or more portions of tissue to form the adhesive pin fastener therein.

6. The surgical device of claim 1 wherein the fastener forming end effector includes one or more hollow needles reciprocatably mounted within the first jaw to penetrate into and retract from the one or more portions of tissue clamped within the first jaw and the second jaws.

7. The surgical device of claim 6 wherein each of the one or more hollow needles have a sharp edge for coring a passage through the one or more portions of tissue and a hollow for storing the tissue remnants therein.

8. The surgical device of claim 7 wherein the one or more hollow needles have a reciprocating plunger within the hollow for ejecting the tissue remnants from each of one or more hollow needles the hollow needle and into one of the first head forming pocket and the second head forming pocket, the tissue remnants becoming encapsulated in the adhesive pin fastener when the fluid polymer adhesive is formed.

9. The surgical device of claim 8 wherein the one or more hollow needles and the plunger mounted within the hollow bends within the first jaw towards the second jaw to penetrate tissue clamped therebetween.

10. The surgical device of claim 6 wherein the one or more hollow needles have a distal point for penetrating tissue and the hollow is filled with the fluid polymer adhesive, wherein when the one or more hollow needles reciprocates to penetrate tissue, the fastener forming end effector dispenses the polymer adhesive from the one or more hollow needles to form a double headed adhesive pin fastener from each of the one or more hollow needles by forming the first fastener head within the first head forming pocket and forming an adhesive shank within the tissue and forming the second fastener head within the second head forming pocket.

11. The surgical device of claim 10 further comprising a knife operatively attached to the one or more hollow needles to penetrate into and cut tissue when the one or more hollow needles penetrate into and retract from the one or more portions of tissue clamped within the first jaw and the second jaws.

12. The surgical device of claim 11 wherein the knife is circular and the one or more hollow needles are in a circular array about the knife.

13. A surgical device for forming fasteners within one or more portions of tissue comprising:
   a) a shaft having a proximal and a distal end;
   b) fluid polymer adhesive contained within the shaft wherein the polymer adhesive is polymerized by exposure to an adhesive initiator; and
   c) a fastener forming end effector at a distal end of the shaft configured to form an adhesive pin fastener in the one or more portions of tissue with the fluid polymer adhesive, wherein the fluid polymer adhesive is shaped into the adhesive pin fastener from at least a portion of the distal end of the shaft and polymerized by exposing the shaped fluid polymer adhesive to the adhesive initiator, wherein the fastener forming end effector comprises two head forming features positionable on opposite sides of the one or more portions of tissue, wherein the fastener forming end effector is operable to dispense the fluid polymer adhesive into each of the two head forming features such that the adhesive pin fastener formed by the fastener forming end effector has two heads, each head being positioned on opposite sides of the one or more portions of tissue.

14. The surgical device of claim 13 wherein the adhesive initiator is one selected from the group consisting of tissue contact, heat, moisture, and polymerization initiating compounds.

15. A surgical device of claim 13 wherein the fastener forming end effector comprises at least one hollow needle reciprocatably reciprocally mounted within the shaft and filled with the fluid polymer adhesive, wherein reciprocation of the at least one hollow needle drives the hollow needle into tissue and retraction of the needle dispenses the fluid polymer adhesive into the one or more portions of tissue as the needle retracts.

16. A surgical device of claim 14 including a plunger within the at least one hollow needle for dispensing the fluid polymer adhesive from the at least one hollow needle during reciprocation of the hollow needle.

* * * * *